United States Patent [19]
Wobbe et al.

[11] Patent Number: 6,165,998
[45] Date of Patent: Dec. 26, 2000

[54] ANTIFUNGAL AGENTS

[75] Inventors: C. Richard Wobbe, Lexington; John D. Bradley, Brookline; Zhe Li, Malden, all of Mass.

[73] Assignee: Scriptgen Pharmaceuticals, Inc., Waltham, Mass.

[21] Appl. No.: 09/153,202

[22] Filed: Sep. 15, 1998

Related U.S. Application Data

[60] Provisional application No. 60/058,802, Sep. 15, 1997.

[51] Int. Cl.$^7$ .......................... A61K 31/05; A61K 31/165; A61K 31/275; A61K 31/655; A61K 31/69
[52] U.S. Cl. ............................ 514/150; 514/622; 514/733
[58] Field of Search .................................... 514/150, 622, 514/733

[56] References Cited

U.S. PATENT DOCUMENTS

| | | | |
|---|---|---|---|
| 3,238,189 | 3/1966 | May et al. | 534/660 |
| 3,331,874 | 7/1967 | Stecker | 564/214 |
| 5,512,451 | 4/1996 | Kricka | 435/28 |

FOREIGN PATENT DOCUMENTS

| | | |
|---|---|---|
| 4-230739 | 8/1992 | Japan . |
| 5-107570 | 4/1993 | Japan . |
| 5-241211 | 9/1993 | Japan . |

OTHER PUBLICATIONS

Kracker et al., Chemical Abstracts, 51:12499i, "Fast Yellow Dyeings on Polyester Fibers", 1957.
Higashino , Chemical Abstracts, 53:10096e, "Antifungal Properties of Azophenol Derivatives", 1959.
Yamazoe, Chemical Abstracts, 54:17699b, "Experimental Chemotherapy for Dermatomycosis and Candidiasis. I Antifungal Activity of Various Azophenol Compounds In Vitro", 1960.
Hayashi et al., Chemical Abstracts55:27651g, "Anthelmintics. IX. The Actions of Azophenol and Azothymol Derivatives on Earthworm and on Intestinal Parasites of Animals", 1961.
Yamazoe et al., Chemical Abstracts, 57:9959c, "Experimental Chemotherapy for Dermatomycosis and Candidiasis. II. Antifungal Activity of Various p–Arylazopphenol Compounds In Vitro", 1962.
Chemical Abstracts, The American Chemical Society, Aug. 25, 1957, vol. 51, No. 16, the abstract No. 12500d, Fast Yellow Dyeings on Polyester Fibers', DE 965,395, (Farbwerke Hoechst A.–G. Vorm. Meister Lucius & Bruning) Jun. 6, 1957.
Chemical Abstracts, The American Chemical Society, Apr. 30, 1973, vol. 78, No. 17, the abstract No. 110729n, Fialkov, Y.A. et al., "Hydrolysis of a Trifluoromethyl Group Bound to a Conjugated Aromatic System, III. Hydrolysis of the Trifluoromethyl Group in Stilbene, Tolan, and Azobenzene Derivatives." Zh Org. Khim 1973, 9(1), 138–43 (Russ).
Bashir, et al., Planta Med 57:2, 192–3, Monnina, Apr. 1990.
Inamori, et al., Chem Pharm Bull (Tokyo) 32; 2, 801–4, Feb. 1984.

Lorimer, et al., Journal Of Natural Products, vol. 56, No. 9, pp. 1444–1450, Sep. 1993.
Schultz, et al., Phytochemistry vol. 30: No. 9, pp. 2939–2945, 1991.
Zbaida, et al., Drug Metab Dispos 22: 3, 412–8, May–Jun. 1994.
Stefancich, et al., II Farmaco 48 (8) 1103–112, 1993.
Drobnica, et al., American Society For Microbiology, vol. 16, 1968.
Goodman, et al., Natl Cancer Inst. 73: 1, 265–73, Jul. 1984.
Andrews, et al., Carcinogenesis 11: 9, 1551–6, Sep. 1990.
Stoddart, et al., Drug Metab Dispos 18: 1, 36–41, Jan.–Feb. 1990.
Sweeney, et al., Environ Health Perspect 102, Suppl 6: 119–22, Oct. 1994.
Takahashi, et al., Structure Determination, J. Antibiot (Tokyo) 42: 11, 1541–6, Nov. 1989.
Koh, et al., Drug Metabol Drug Interact 7: 4, 273–85, 1989.
Koh, et al., Drug Metabol Drug Interact 7: 4, 253–72, 1989.
Boido, et al., Farmaco 48: 6, 749–75, Jun. 1993.
Schwaller, et al., Anal Biochem 177: 1, 183–7, Feb. 15, 1989.

(List continued on next page.)

*Primary Examiner*—Fiona T. Powers
*Attorney, Agent, or Firm*—Darby & Darby

[57] ABSTRACT

The present invention provides azo and stilbene compounds having the structure:

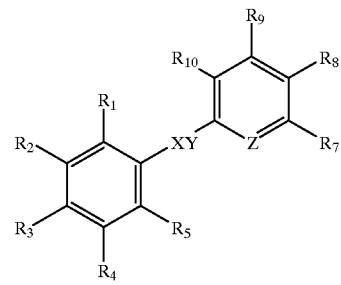

wherein XY is N=N, CH=CH, (C=O)—NH or NH—(C=O); wherein Z is CR$_6$ or N; wherein R$_1$, R$_2$ and R$_5$ are independently hydrogen, halogen, NO$_2$ or CF$_3$; wherein R$_3$ is hydrogen, halogen, CF$_3$, aryl or heteroaryl, NO$_2$ or OCF$_3$; wherein R$_4$ is hydrogen, halogen, CF$_3$, aryl or heteroaryl, NO$_2$ or linear or branched chain alkoxy; wherein R$_6$ is hydrogen or linear or branched alkyl; wherein R$_7$ is hydrogen, cyano, hydroxyalkyl, carboxyl, halogen, hydroxyl, formyl, NO$_2$ or halogen; and wherein R$_8$ is hydroxyl or substituted or unsubstituted amino; and wherein R$_9$ and R$_{10}$ are independently hydrogen, CN or hydroxyalkyl. Said compounds are useful as antifungal therapeutics, fungicides and fungistats. The present invention also provides methods of inhibiting fungal RNA transcription and treating fungal infections in human and animal subjects and fungal infestations in plants.

7 Claims, 26 Drawing Sheets

OTHER PUBLICATIONS

Li, et al., Cancer Lett 56:1, 17–2 Jan. 1991.
Kuroda, et al., Chem Pharm Bull, Tokyo 37: 5, 1345–6, May 1989.
Hasegawa, et al., J Comput Aided Mol Des 8: 4, 449–56, Aug. 1994.
Awad, et al., J. Chem Tech. Biotechnol. 1992, 55–217–225.
Langcake, et al., J. Chem. Soc., Chem. Commun. 1977, (7), 208–10 (abstract).
Langcake, et al., Experientia, 1977, 33(2), 151–2 (abstract).
Ward, et al., Can. J. Bot., 1975, 53(10), 964–71 (abstract).
Alcubilla, et al., Eur. J. Forest Pathol. 1972, 1(2), 100–14 (abstract).
Pryce, R.J., Phytochemisry, 1972, 11(4), 1355–64 (abstract).
Drobnica, et al., Appl., Microbiol, 1968, 16(4), 582–7 (abstract).
Hasegawa, et al., Journal of Computer–Aided Molecular Design, 1994 Aug., 8(4) 449–56 (abstract).
Canu Boido, et al., Farmaco, Jun. 1993, 48 (6) 749–75 (abstract).
Awad, et al., Journal of Chemical Technology and Biotechnology, 1992, 55 (3) 217–25 (abstract).
Zaprutko, et al., Pharmazie, Apr. 1992, 47 (4) 258–61 (abstract).
Awad, Journal of Chemical Technology And Biotechnology, 1992, 53 (3) 227–36 (abstract).
Ibrahim, et al., Journal of Inorganic Biochemistry, Jul. 1991, 43 (1) 1–7 (abstract).
Takahashi, et al., Journal Of Antibiotics, Nov. 1989, 42 (11) 1541–6 (abstract).
Nakayama, et al., Journal Of Antibiotics, Nov. 1989, 42 (11) 1535–40 (abstract).
Mitrofanov, et al., Antibiotiki I Meditsinskaia Biotekhnologiia, Jan. 1986, 31 (1) 136 (abstract).
Wegmann, Immunitat Und Infektion, Aug. 1984, 12 (4) 181–5 (abstract).
Schauerte, et al., Ecotoxicology And Environmental Safety, Dec. 1982, 6 (6) 560–9 (abstract).
Awasthi, et al., Zenralblatt Fur Mikrobiologie, 1982, 137 (6) 503–7 (abstract).
Imre, et al., Zeitschrift Fur Versuchstierkunde, 1980, 22 (4) 230–3 (Title Only).
Vigfusson, et al., Mutation Research, Sep. 1980, 79 (1) 53–7 (abstract).
Zsolnai, Zentralblatt Fur Bakteriologie, Parasitenkunde, Infektionskrankheiten Und Hygiene, Erste Abteilung Originale, Reihe A: Medizinische Mikrobiologie Und Parasitologie, Apr. 1978, 240 (3) 385–7 (abstract).
Nigro, et al., Cancer Research, Sep. 1977, 37 (9) 3198–203 (Title Only).
Umezawa, et al., Journal of Antibiotics, Jan. 1975, 28 (1) 87–90 (Title Only).
Schewe et al., Acta Biologica Et Medica Germanica, 1974 32 (5) 419–26 (Title Only).
Karanth, et al., Applied Microbiology, Jan. 1974, 27 (1) 43–6 (Title Only).
Moss, et al., Journal Of The American Chemical Society, Jun. 14, 1972, 94 (12) 4392–4 (Title Only).
Kosower, et al., Journal Of Medicinal Chemistry, Mar. 1972, 15 (3) 307–12 (Title Only).
Sijpesteijn, et al., Annals Of Applied Biology, Jun. 1968, 61 (3) 473–9 (Title Only).
Fields, et al., Journal Of Medicinal Chemistry, Nov. 1970, 13 (6) 1243–3 (Title Only).
Brans, et al., Journal Of The Chemical Society, Perkin Transactions 1, 1970, 2 225–7 (Title Only).
Hamada, et al., Yakugaku Zasshi. Journal Of The Pharmaceutical Society Of Japan, Sep. 1968, 88 (9) 1097–102 (Title Only).
Drobnica, et al., Applied Microbiology, Apr. 1968, 16 (4) 582–7 (Title Only).
Morehart, et al., Applied Microbiology, Sep. 1967, 15 (5) 1248–51 (Title Only).
Zsolnai, Biochemical Pharmacology, Oct. 1965, 14 (10) 1425–44 (Title Only).
Zsolnai, Biochemical Pharmacology, Sep. 1965, 14 (9) 1325–62 (Title Only).
Zsolnai, Zentralblatt Fur Bakteriologie, Parasitenkunde, Infedtionskrankheiten Und Hygiene. 1 Abt. Medizinisch–Hygienische Bakteriologie Virusforschung Und Parasitologie. Originale, Apr. 1965, 196 (1) 95–115 (Title Only).
Gopal, et al., Indian J. Heterocycl. Chem. 1996, 6 (1), 49–52 (abstract).
Awad, Phosphorus, Sulfur Silicon Relat. Elem. 1996, 114 (1–4), 17–28 (abstract).
Sayed, Al–Azhar J. Pharm. Sci. 1994, 14, 108–15 (abstract).
Suman, et al., Indian J. Chem., Sect. B: Org. Chem. Incl. Med. Chem.(1995), 34B (8), 743–46 (abstract).
Nesterova, et al., Khim.–Farm. Zh. 1993, 27 (2), 33–6 (abstract).
Nasef, et al., Egypt. J. Chem 1992, vol. Date 1991, 34 (4), 335–46 (abstract).
Nakata, et al., Tetrahedron Lett. 1993, 34 (38), 6095–8 (abstract).
Toshkhodzhaev, et al., Izv. Vyssh. Uchen. Zaved., Khim. Khim. Tekhnol. (1993), 36 (3) 97–101 (abstract).
Abdel, et al., J. Chin. Chem. Soc., Taipei 1993, 40 (3), 289–96 (abstract).
Awad, et al., J. Chem. Biotechnol, 1992, 55 (3), 217–25 (abstract).
Awad, Bull. Chem. Soc. Jpn. 1993, 66 (1), 167–73 (abstract).
Komaritsa, et al., Farm. Zh. Kiev, 1992, (4), 39–43 (abstract).
Awad, J. Chem. Technol. Biotechnol. 1992, 53 (3), 227–36 (abstract).
Jolly, et al., J. Indian Chem. Soc. 1991, 68 (9) 513–14 (abstract).
Hanna, et al., J. Chem. Technol. Biotechnol. 1991, 52 (4), 559–70 (abstract).
Awad, Dyes Pigm. 1991, 17 (2), 123–9 (abstract).
Johnson, et al., Book Pap.–Int. Conf. Exhib., AATCC 1989, 70–4 (abstract).
Nesterova, et al., Khim.–Farm.Zh. 1990, 24 (11), 36–40 (abstract).
Portnov, et al., Khim.–Farm. Zh. 1990, 24 (11), 34–6 (abstract).
Eisa, et al., Pak. J. Sci. Ind. Res. 1988, 31 (7), 474–6 (abstract).
Ergenc, et al. Pharmazie 1989, 44 (8), 573–4 (abstract).
Radl, et al., Cesk. Farm. 1989, 38 (3) 114–17 (abstract).
Platonova, et al., SB. Nauch. Tr. Ryazan. Med. In–T, 1987, 92 53–8 (Title Only).
Ahluwalia, et al., Indian J. Chem., Sec. B. 1987, 26B (7), 697–9 (abstract).
El–Nasser Ossman, et al., Bull. Pharm. Sci., Assiut Univ. 1986, 9 (1), 89–104 (abstract).
Ames, et al., J. Free Radicals Biol. Med. (1986), 2 (5–6), 377–91 (abstract).

Popova, et al., Khim–Farm Zh., 1987, 21 (1), 49–52 (abstract).
Ergenc, et al., Arch. Pharm. (Weinheim, Ger.), 1986, 319 (6), 545–9 (abstract).
Mitrofanov, et al., Antibiot. Med. Biotekhnol., 1985, 31 (1), 13–16 (abstract).
Popova, et al., Farm. Zh. (Kiev), 1985, (6), 41–4 (abstract).
Tanaka, et al., Chem. Pharm. Bull. 1984, 32 (8), 3291–8 (abstract).
Rao, et al., Curr. Sci., 1984, 53 (15), 799–800 (abstract).
Marko, et. al., ZB.PR. Chemickotechnol. Fak. Svst, 1981, vol. Date 1977–78, 253–9 (abstract).
Lipthay, et al., ACTA FAC. Rerum Nat. Univ. Comenianae, Chim., 1981, 29, 9–15 (abstract).
Habib, et al., Sci. Pharm. 1981, 49 (1) 42–51 (abstract).
Lipthay, et al., ACTA FAC, Rerum Nat. Univ. Comenianae, Chim., 1980, 28, 137–44 (abstract).
Lipthay, et al., ACTA FAC, Rerum Nat. Univ. Comenianae, Chim., 1979, 27, 125–32 (abstract).
Jolly, et al., Indian J. Chem, Sect. B. 1978, 16B (12), 1117–18 (abstract).
Akramova, et al., Deposited Doc., 1976, Viniti 4406–76, 6pp. (abstract).
Shams El–Dine, et al., Sci. Pharm, 1978, 46 (3) 194–200 (abstract).
Habib, et al., Sci. Pharm., 1977, 45 (4), 310–14 (abstract).
Zsolnai, Zentralbl. Bakteriol., Parasitenkd, Infektionskr. Hyg., ABT. 1: Orig., Reihe A 1978, 240 (3), 385–7 (abstract).
Korshunova, et al., SB. Nauch. TR. Magnitogorsk. Gornometallurg. IN–T 1975, 152, 33–6 (Title Only).
Mehrotra, et al., Colourage (1976, 23 (9A), 19–21 (abstract).
Mehrotra, et al., Colourage 1975, 22 (25), 17–19 (abstract).
Mehrotra, et al., Colourage 1975, 22 (16), 25–8 (abstract).
Mehrotra, et al., Colourage, 1975, 22 (8) 25–31 (abstract).
Chandra, et al., J. Indian Chem., 1974, 51 (4), 524–6 (abstract).
Nesynov, et al., Fiziol. Aktiv. Veshchestva, 1973, 5, 63–7 (abstract).
Eckhard, et al., Aust. J. Chem., 1973, 26 (12), 2705–10 (abstract).
Mitra, et al., Labdev, Part A, 1972, 10 (3–4) 154–8 (abstract).
Srivastava, et al., Indian J. Appln. Chem, 1969, 32 (2), 107–15 (abstract).
Mitra, et al., Labdev, Part B, 1968, 6 (4) 223–5 (abstract).
Daniel, Biochem J., 1969, 111 (5), 695–702 (abstract).
Mitra, et al., Labdev, Part A, 1968, 6 (3), 140–3 (abstract).
Frankovskii, et al., TR. Leningrad, Khim.–Farm. Inst., 1967, No. 22, 144–50 (abstract).
Fox, et al., Ann. Appl. Biol., 1963, 52 (1), 33–44 (abstract).
Srivastava, Curr. Sci., 1968, 37, (11), 315–16 (abstract).
Matolcsy, Acta Pharm. Hung., 1968, 38 (2–3), 133–5 (abstract).
Frankovskii, et al., Zh. Org. Khim., 1967, 3 (10), 1839–43 (abstract).
Talukdar, et al., J. Indian Chem. Soc., 1967, 44 (2), 104–9 (abstract).
Gaind, et al., Indian J. Pharm., 1966, 28 (10), 272–4 (abstract).
Sehra, et al., J. Sci. Technol. (Aberdeen, Scotl), 1966, 4 (2), 75–85 (abstract).
Hain, et al., Nature, 1993 Jan. 14, 361, (6408) 153–6 (abstract).
Pearce, Physiol. Mol. Plant Pathol., 1996, 48 (2), 117–29 (abstract).
Pettit, et al., J. Med., Chem., 1995, 38 (15), 2994 (abstract).
Mattivi, et al., Bull. Liaison—Groupe Polyphenols, 1992, 16 (Pt. 1), 116–19 (abstract).
Pettit, et al., J. Med. Chem., 1995, 38 (10), 1666–72 (abstract).
Pearce, et al., Plant, Cell Environ., 1995, 18 (3), 303–7 (abstract).
Bowyer, et al., J. Pharmacol, Exp. Ther., 1993, 266 (2), 1066–74 (abstract).
Nussbaumer, et al., J. Med., Chem., 1993, 36 (15), 2115–20 (abstract).
Schultz, et al., Phytochemistry, 1992, 31 (11), 3801–6 (abstract).
Schultz, et al., Phytochemistry, 1991, 30 (9), 2939–45 (abstract).
Maillard, et al., Helv. Chim. Acta (1991), 74 (4), 791–9 (abstract).
Underwood, et al., Phytochemistry, 1991, 30 (7), 2183–9 (abstract).
Dikshit, et al., Nat'l. Acad. Sci. Lett., (India), 1990, 13 (2) 43–5 (abstract).
Asakawa, et al., Phytochemistry, 1991, 30 (1) 219–34 (abstract).
Inamori, et al., Chem. Pharm. Bull., 1991, 39 (1), 218–20 (abstract).
Pont, et al., J. Phytopathol, 1990, 130 (1), 1–8 (abstract).
Schultz, et al., Phytochemistry, 1990, 29 (5), 1501–7 (abstract).
Jeandet, et al., Bull. O.I.V., 1989, 62 703–704, 637–57 (abstract).
Sugihara, Nippon Kasei Gakkaishi, 1989, 40 (8), 691–6 (abstract).
Adesanya, et al., Phytochemistry, 1989, 28 (3), 773–4 (abstract).
Moreno–Manas, et al., J. Heterocycl., Chem. 1988, 25 (5), 1439–41 (abstract).
Arnoldi, et al., J. Agric. Food Chem., 1989, 37 (2), 508–12 (abstract).
Woodward, et al., Physiol. Mol. Plant Pathol., 1988, 33 (1) 127–49 (abstract).
Hashimoto, et al., Phytochemistry, 1988, 27 (1), 109–13 (abstract).
Inamori, et al., Chem. Pharm. Bull., 1987, 35 (8), 3502–6 (abstract).
Castro, et al., J. Nat. Prod., 1986, 49 (4), 680–3 (abstract).
Inamori, et al., Chem. Pharm. Bull., 1985, 33 (7), 2904–9 (abstract).
Inamori, et al., Chem. Pharm. Bull., 1984, 32 (2), 801–4 (abstract).
Chi, et al., Yakhak Hoe Chi, 1983, 27 (1), 37–43 (abstract).
Patratii, et al., Khim,–Farm. Zh., 1982, 16 (1), 67–70 (abstract).
Raynal, et al., Ann Phytopathol., 1980, 12 (3), 163–75 (abstract).
Gorham, Prog. Phytochem., 1980, 6, 203–52 (abstract).
Langcake, et al., Vitis, 1979, 18 (3), 244–53 (abstract).
Takasugi, et al., Chem. Lett., 1978, 11, 1241–2 (abstract).
Goghari, et al., J. Indian Chem. Soc., 1977, 54 (6), 621–2 (abstract).
Pryce, et al., Phytochemistry, 1977, 16 (9), 1452–4 (abstract).

R. Nakajima, et al., "In Vitro and In vivo Antifungal Activities of DU–6859a, a Fluoroquinolone, in Combination with Amphotericin B and Fluconazole Against Pathogenic Fungi," Antimicrobial Agents and Chemotherapy, Jul. 1995, pp. 1517–1521.

A. Geber, et al., "Deletion of the *Candida glabrata* ERG3 and ERG 11 Genes: Effect on Cell Viability, Cell Growth, Sterol Composition, and Antifungal Susceptibility," Antimicrobial Agents and Chemotherapy, Dec. 1995, pp. 2708–2717.

S. Heidler, et al., "The AURI gene in *Saccharomyces cerevisiae* Encodes Dominant Resistance to the Antifungal Agent Aureobasidin A (LY295337)," Antimicrobial Agents and Chemotherapy, Dec., 1995, pp. 2765–2769.

H. Wardle, et al., "In Vitro Activity of BMS–181184 Compared with Those of Fluconazole and Amphotericin B against Various Candida spp," Antimicrobial Agents and Chemotherapy, Sep. 1996, pp. 2229–2233.

K. Hata, et al., "in Vitro and In Vivo Antifungal Activities of ER–30346, a Novel Oral Triazole with a Broad Antifungal Spectrum," Antimicrobial Agents and Chemotherapy, Oct. 1996, p. 2237–2242.

K. Hata, et al., "Efficacy of ER–30346, a Novel Oral Triazole Antifungal Agent, in Experimental Models of Aspergillosis, Candidiasis, and Cryptococcosis," Antimicrobial Agents and Chemotherapy, Oct. 1996, pp. 2243–2247.

D. Sanglard, et al., "Susceptibilities of *Candida albicans* Multidrug Transporter Mutants to Various Antifungal Agents and Other Metabolic Inhibitors," Antimicrobial Agents and Chemotherapy, Oct. 1996, pp. 2300–2305.

E. Anaissie, et al., "Microdilution Antifungal Susceptibility Testing of *Candida albicans* and *Cryptococcus neoformans* with and without Agitation: an Eight–Center Collaborative Study," Antimicrobial Agents and Chemotherapy, Oct. 1996, pp. 2387–2391.

K. Venkateswarlu, et al., "Reduced Accumulation of Drug in *Candida krusei* Accounts for Itraconazole Resistance," Antimicrobial Agents and Chemotherapy, Nov. 1996, pp. 2443–2446.

A. Yotsuji, et al., "T–8581, a New Orally and Parenterally Active Triazole Antifungal Agent: In Vitro and In Vivo Evaluations," Antimicrobial Agents and Chemotherapy, Jan. 1997, pp. 30–34.

J. Galgiani, et al., "In Vitro Studies of Activities of the Antifungal Triazoles SCH56592 and Itraconazole Against *Candida albicans*, *Cryptococcus neoformans*, and Other Pathogenic Yeasts," Antimicrobial Agents and Chemotherapy, Jan. 1997, pp. 180–183.

M. Watanabe, et al., "The In–vitro Activity of an Antifungal Antibiotic Benanomicin A in Comparison with Amphotericin B," Journal of Antimicrobial Chemotherapy (1996), 38, 1073–1077.

K. Ohtsuka, et al., "The in–vitro activity of an antifungal antibiotic, benanomicin A, in comparison with amphotericin B and fluconazole," Journal of Antimicrobial Chemotherapy (1997) 39, 71–77.

D. Lamb, et al., "The Mutation T315A in *Candida albicans* Sterol 14α–Demethylase Causes Reduced Enzyme Activity and Fluconazole Resistance Through Reduced Affinity,"The Journal of Biological Chemistry, vol. 272, No. 9, Issue of Feb. 28, pp. 5682–5688 1997.

A. Espinel–Ingroff, et al., "Multicenter Evaluation of Proposed Standardized Procedure for Antifungal Susceptibiilty Testing of Filamentous Fungi," Journal of Clinical Microbiology, Jan. 1997, p. 139–143, vol. 35, No. 1.

N. Gresh, et al., "A Theoretical Study of the Nonintercalative Binding of Berenil and Stilbamidine to Double–Stranded $(dA–dT)_n$ Oligomers," Molecular Pharmacology, 25:452–458.

I. Kubo, et al., "Combination Effects of Antifungal Nagilactones Against *Candida Albicans* and Two Other Fungi With Phenylpropanoids," Journal of Natural Products, vol. 56, No. 2, pp. 220–226, Feb. 1993.

G. Schröder, et al., "Molecular Analysis of Resveratrol Synthase cDNA, Genomic Clones and Relationship With Chalcone Synthase," Eur. J. Biochem. 172, 161–169 (1988).

J. Miller, "Stilbamidine: *tempus fugitl*," New York State Journal of Medicine p. 6, Jan., 1984.

Hans–Guenter Neumann, "The role of DNA Damage in Chemical Carcinogenesis of Aromatic Amines," J. Cancer Res. Clin Oncol (1986) 112: 100–106.

B. Epe, J. Hegler and M. Metzler, "Site–specific Covalent Binding of Stilbene–Type and Steroidal Estrogens to Tubulin Following Metabolic Activation in Vitro," Carcinogenesis, vol. 8, No. 9, pp. 1271–1275, 1987.

M. Palangat, et al., "Organ–Specific Inhibition of Types I, II and II Transcriptional Activity in Hamsters Exposed to Stilbene Estrogen," Carcinogenesis, vol. 16, No. 5, pp. 1017–1021, 1995.

A. Gladek, et al., "Transplacental Genotoxicity of Diethylstilbestrol," Carcinogenesis, vol. 12, No. 5, pp. 773–776, 1991.

B. Moorthy, et al., "Evidence from $^{32}$P–Postlabeling and the Use of Pentachlorophenol for a Novel Metabolic Activation Pathway of Diethylstilbestrol and Its Dimethyl Ether in Mouse Liver; Likely α–Hydroxylation of Ethyl Group(s) Followed by Sulfate Conjugation," Carcinogenesis, vol. 16, No. 11, pp. 2643–2648, 1995.

H. Bhat, et al., "Regulation of the Formation of the Major Diethylstilbestrol–DNA Adduct and Some Evidence of its Structure". Carcinogenesis, vol. 15, No. 10, pp. 2137–2142, 1994.

J. Fostel, et al., "Comparison of Responses of DNA Topoisomerase I from *Candida Albicans* and Human Cells to Four New Agents Which Stimulate Topoisomerase–Dependent DNA Nicking," FEMS Microbiology Letters, 138 (1996) 105–111.

K. Zakrzewska, et al., "The Solvation Contribution to the Binding Energy of DNA With Non–Intercalating Antibiotics," Nucleic Acid Research, vol. 12, No. 16, 1984.

M. Rodriguez, et al., "Relationship Between Structure and Biological Activity of Novel R106 Analogs," The Journal of Antibiotics, vol. 49, No. 4, pp. 386–389.

D. Frost, et al., "Characterization of a Lipopeptide–Resistant Strain of *Candida Albicans*," Can. J. Microbiol. 43: 122–128 (1997).

D. Sanglard, et al., "Cloning of *Candida Albicans* Genes Conferring Resistance to Azole Antifungal Agents: Characterization of CDR2, a New Multidrug ABC Transporter Gene," Microbiology (1997), 143, 405–416.

D. Roy, et al., "Catalysis of the Oxidation and Reduction Reactions of Steroid and Stilbene Estrogens by Nuclear Enzymes," Archives of Biochemistry and Biophysics, vol. 315, No. 2, Dec., pp. 310–316, 1994.

J. Nelson, et al., "Incorporation of a Non–Nucleotide Bridge Into Hairpin Oligonucleotides Capable of High–Affinity Binding to the Rev Protein of HIV–1," Biochemistry 1996, 35, 5339–5344.

J.C. Cubria, et al., "Aromatic Diamidines Are Reversible Inhibitors of Porcine Kidney Diamine Oxidase," Biochemical Pharmacology, vol. 45, No. 6, pp. 1355–1357, 1993.

R. Reguera, et al., "Putrescine Uptake Inhibition by Aromatic Diamidines in *Leishmania Infantum* Promastigotes," Biochemical Pharmacology, vol. 47, No. 10, pp. 1859–1866, 1994.

E. Schoenbach, et al., "The Pharmacology, Mode of Action and Therapeutic Potentialities of Stilbamidine, Pentamidine, Propamidine and Other Aromatic Diamidines—A Review," Medicine 27: 327–377, 1948.

J. Perfect, et al., "In Vitro and In Vivo Efficacies of the Azole SCH56592 Against *Cryptococcus neoformans*", Antimicrobial AGents and Chemotherapy, Aug. 1996, pp. 1910–1913.

| Compound | IC50, μM | | | | MIC, μg/ml |
|---|---|---|---|---|---|
| | Cand. Pol II | Asp. Pol II | Sacch. Pol II | Human Pol II | Cand. Pol III | C. albicans |
| α-amanitin | 20 | >500 | 3.3 | 0.002 | >500 | >100 |
| 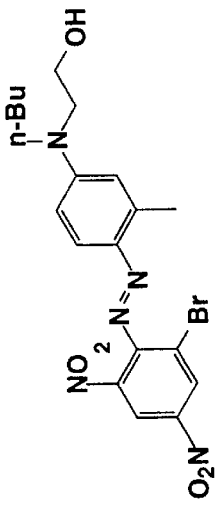 | 4.1 | 6.7 | 4.3 | 12.0 | 13.5 | 40-80 |
|  | 5.8 | 8.0 | 5.8 | 61 | 60.0 | >100 |
| 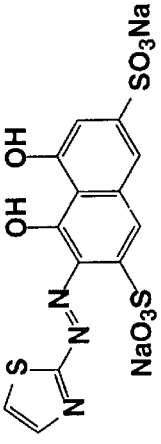 | 0.15 | 0.13 | 0.21 | 1.2 | 0.63 | >100 |
|  | 1.4 | 3.1 | 0.7 | 7.1 | 0.7 | 10-20† |
| 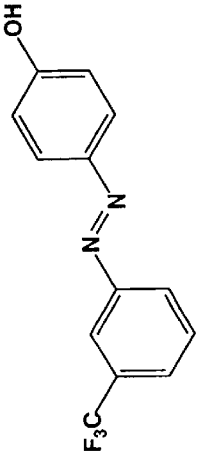 | 15 | 6.9 | 10.0 | 90 | 95.0 | 10-20† |
FIG. 6

FIG. 8

| Species | Isolates | Resistance | MIC, μg/ml |
|---|---|---|---|
| Candida albicans | 4 | | 8-25 |
| | 3 | Azole | 10-50 |
| | 1 | AmpB | 8 |
| Candida tropicalis | 2 | | 8-20 |
| | 1 | AmpB | 10-20 |
| Candida parapsilosis | 2 | | 16-32 |
| Candida kefyr | 1 | | 16-32 |
| Candida glabrata | 1 | | 16 |
| Candida krusei | 1 | | 8 |
| Aspergillus fumigatus | 4 | | 10-32 |
| Aspergillus flavus | 1 | | 20 |
| Cryptococcus neoformans | 7 | | 1-12.5 |
| Histoplasma capsulatum | 1 | | 2.5 |
| Coccidiodes immitis | 1 | | 5 |
| Blastomyces dermatitidis | 1 | | 10 |
| Pseudallescheria boydii | 1 | AmpB | 0.25 |
| Trichophyton quinckeanum | 1 | | 0.063 |
| Trichophyton rubrum | 2 | | 5 |
| Trichophyton mentagrophytes | 2 | | 3-10 |
| Epidermophyton floccosum | 1 | | 5 |
| Fusarium culmorum | 1 | | 5-10 |
| Saccharomyces cerevisiae | 4 | | 2-20 |

FIG. 17

| Species | Isolates | Resistance | MIC, µg/ml |
|---|---|---|---|
| Candida albicans | 3 | | 8-12.5 |
| Candida tropicalis | 2 | Azole | 12.5-32 |
| Candida parapsilosis | 1 | | 8 |
| Candida glabrata | 1 | | 16 |
| Candida krusei | 1 | | 8 |
| Aspergillus fumigatus | 2 | AmpB | 8-12.5 |
| Cryptococcus neoformans | 3 | | 40-64 |
| Histoplasma capsulatum | 7 | | 0.5-10 |
| Coccidiodes immitis | 1 | | 2.5 |
| Blastomyces dermatitidis | 1 | | 10 |
| Trichophyton quinckeanum | 1 | | 20 |
| Trichophyton rubrum | 2 | | 0.5 |
| Trichophyton mentagrophytes | 1 | | 5 |
| Epidermophyton floccosum | 1 | | 10 |
| Fusarium culmorum | 1 | | 5 |
| Saccharomyces cerevisiae | 1 | | 6.25 |
| | 1 | | 2 |

FIG. 21

|  | C. albicans | | C. tropicalis | | C. parap. | C. kefyr |
|---|---|---|---|---|---|---|
|  | WT | keto^r | WT | AmB^r | | |
| Compound 2 | 80 | 80 | 80 | 80 | ND | ND |
| + AmB (sub-MIC) | 1-2 | 1-2 | 1-2 | 80 | ND | ND |

\* Minimal inhibitory concentrations (MIC) were tested in a broth dilution assay by the NCCLS M27P method.

ANTIFUNGAL AGENTS

This application claims priority under 35 U.S.C. § 119 from U.S. provisional patent application Ser. No. 60/058,802, filed Sep. 15, 1997 the disclosure of which is incorporated herein by reference in its entirety.

FIELD OF THE INVENTION

The present invention is in the field of synthetic antifungal agents. In particular, the present invention relates to novel azo and stilbene compounds and related compounds which are useful as antifungal agents. In addition, the present invention provides methods of inhibiting fungal transcription using these compounds.

Throughout this application, various publications are referred to, each of which is hereby incorporated by reference in its entirety into this application to more fully describe the state of the art to which the invention pertains.

BACKGROUND OF THE INVENTION

Gene transcription is the tightly controlled first step in gene expression. In fungi, only one conserved pathway exists for synthesizing mRNA. mRNA synthesis in fungi is carried out in the nucleus only by RNA polymerase II (Pol II), in conjunction with over 20 additional polypeptides that include DNA binding proteins, protein kinase, multiple DNA unwinding activities, and processivity and assembly factors (FIG. 1). Factors involved in fungal transcription differ significantly from the factors controlling human mRNA transcription. For example, the process of transcription initiation differs between yeast and human cells (FIG. 2). A number of exploitable differences between fungal and human nuclear polymerase involved in transcription have been determined. Because gene transcription is highly conserved among fungi and is distinct from mammalian transcription, the present inventors expected inhibitors of fungal RNA polymerase II to be broad spectrum and non-cytotoxic. Due to the uniqueness of the molecular target, fungal transcription inhibitors were also expected to be effective against fungi with acquired resistance to marketed antifungal with different mechanisms of action.

Accordingly, the present inventors have sought out compounds which are able to inhibit fungal transcription processes by inhibition of RNA polymerase II. Pol II consists of 11–12 subunits of which 4 are shared with fungal DNA-dependent RNA polymerase I and III. Pol II was chosen as an antifungal drug discovery target because of its essential role in fungal gene transcription. RNA polymerase II was purified from *Candida albicans, Aspergillus nidulans* and *Saccharomyces cerevisiae* and from human cells. A robust, reproducible high throughput RNA elongation assay using *C. albicans* RNA polymerase II was developed and several novel antifungal agents were identified as potent inhibitors of fungal RNA polymerase II, selective for fungal polymerase IIs relative to human RNA polymerase II.

Screening and counterscreening of a small molecule chemical library have produced a number of potent Pol II inhibitors. Certain of these inhibitors are rapidly fungicidal, with broad spectrum antifungal activity in vitro. Moreover, new compounds which include azo and stilbene analogues of these inhibitors have been prepared which have potent antifungal activity, and which are active against amphotericin- and azole-resistant fungal strains and effective as oral agents in a murine model of systemic *C. albicans* infection.

SUMMARY OF THE INVENTION

One object of the present invention is to provide novel compounds which are capable of inhibiting fungal growth in a subject, including a human subject, an animal or in plants.

Another object of the invention is to provide compounds which are fungistatic or fungicidal against a broad spectrum of fungi.

A further object of the invention is to provide azo compounds, stilbene compounds, as well as other isosteric analogues thereof, which are capable of inhibiting the transcription of mRNA.

A further object of the invention is to provide methods of inhibiting RNA transcription using said novel compounds, either alone or in combination with synergistic agents.

A further object of the invention is to provide methods of treating subjects suffering from fungal infections using the novel compounds disclosed herein, either alone or in combination with synergistic agents such as amphotericin B.

Accordingly, the present invention provides a compound having the structure:

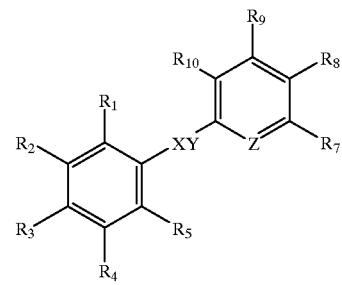

wherein XY is N=N, CH=CH, (C=O)—NH or NH—(C=O); wherein Z is $CR_6$ or N; wherein $R_1$, $R_2$ and $R_5$ are independently hydrogen, halogen, $NO_2$ or $CF_3$; wherein $R_3$ is hydrogen, halogen, $CF_3$, aryl or heteroaryl, $NO_2$ or $OCF_3$; wherein $R_4$ is hydrogen, halogen, $CF_3$, aryl or heteroaryl, $NO_2$ or linear or branched chain alkoxy; wherein $R_6$ is hydrogen or linear or branched alkyl; wherein $R_7$ is hydrogen, cyano, hydroxyalkyl, carboxyl, halogen, hydroxyl, formyl, $NO_2$ or halogen; and wherein $R_8$ is hydroxyl or $NR_{11}R_{12}$; wherein $R_9$ and $R_{10}$ are independently hydrogen, CN or hydroxyalkyl; and wherein $R_{11}$ and $R_{12}$ are independently hydrogen, alkyl, hydroxyalkyl, arylalkyl, hydroxyarylalkyl or aryl.

The present invention further provides a method of inhibiting RNA transcription in a subject which comprises administering an amount of a compound having structure:

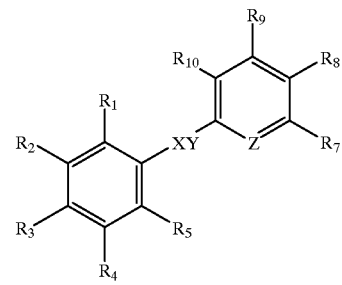

wherein XY is N=N, CH=CH, (C=O)—NH or NH—(C=O); wherein Z is $CR_6$ or N; wherein $R_1$, $R_2$ and $R_5$ are independently hydrogen, halogen, $NO_2$ or $CF_3$; wherein $R_3$ is hydrogen, halogen, $CF_3$, aryl or heteroaryl, $NO_2$ or $OCF_3$; wherein $R_4$ is hydrogen, halogen, $CF_3$, aryl or heteroaryl, $NO_2$ or linear or branched chain alkoxy; wherein $R_6$ is hydrogen or linear or branched alkyl; wherein $R_7$ is hydrogen, cyano, hydroxyalkyl, carboxyl, halogen, hydroxyl, formyl, $NO_2$ or halogen; and wherein $R_8$ is hydroxyl or $NR_{11}R_{12}$; wherein $R_7$ and $R_{10}$ are independently hydrogen, CN or hydroxyalkyl; and wherein $R_{11}$ and $R_{12}$ are independently hydrogen, alkyl, hydroxyalkyl, arylalkyl, hydroxyarylalkyl or aryl; to the subject, said amount being effective to inhibit RNA transcription.

The present invention additionally provides a method of treating a subject suffering from a fungal disease which comprises administering an amount of a compound having the structure:

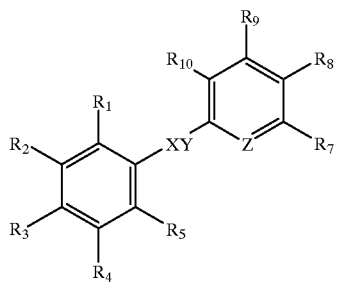

wherein XY is N=N, CH=CH, (C=O)—NH or NH—(C=O); wherein Z is $CR_6$ or N; wherein $R_1$, $R_2$ and $R_5$ are independently hydrogen, halogen, $NO_2$ or $CF_3$; wherein $R_3$ is hydrogen, halogen, $CF_3$, aryl or heteroaryl, $NO_2$ or $OCF_3$; wherein $R_4$ is hydrogen, halogen, $CF_3$, aryl or heteroaryl, $NO_2$ or linear or branched chain alkoxy; wherein $R_6$ is hydrogen or linear or branched alkyl; wherein $R_7$ is hydrogen, cyano, hydroxyalkyl, carboxyl, halogen, hydroxyl, formyl, $NO_2$ or halogen; and wherein $R_8$ is hydroxyl or $NR_{11}R_{12}$; and wherein $R_9$ and $R_{10}$ are independently hydrogen, CN or hydroxyalkyl; and wherein $R_{11}$ and $R_{12}$ are independently hydrogen, alkyl, hydroxyalkyl, arylalkyl, hydroxyarylalkyl or aryl; to the subject, said amount being effective to treat the disease.

BRIEF DESCRIPTION OF THE DRAWINGS

FIG. 6 illustrates preferential fungal pol II inhibitors.

FIG. 8 illustrates the broad spectrum activity of Compound 1.

FIG. 17 illustrates the broad spectrum activity of Compound 6.

FIG. 21 illustrates antifungal synergy of Compound 2 with amphotericin B (Am B).

DETAILED DESCRIPTION OF THE INVENTION

Figure 1:
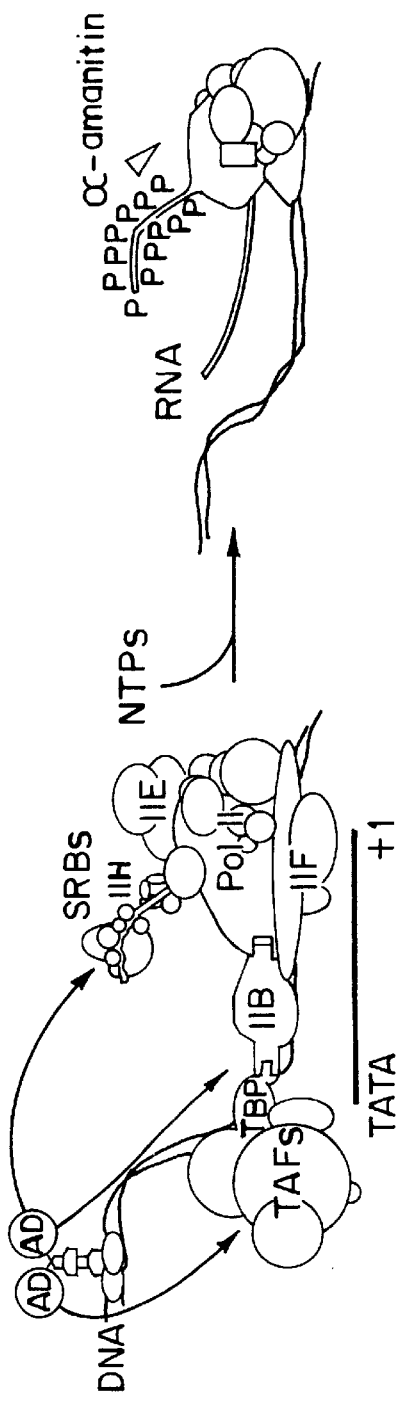
FIG. 1 illustrates protein factors required for initiation of mRNA synthesis in fungi and humans and fungal transcription as a target for antifungal agents.

The present invention provides compounds useful for inhibiting mRNA transcription in fungi and for treating fungal infections such as candidiasis, cutaneous and subcutaneous mycoses as well as plant fungal infections.

The present invention provides a compound having the structure:

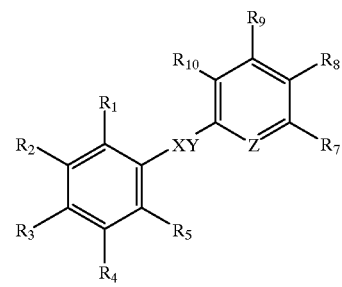

wherein XY is N=N, CH=CH, (C=O)—NH or NH—(C=O); wherein Z is $CR_6$ or N; wherein $R_1$, $R_2$ and $R_5$ are independently hydrogen, halogen, $NO_2$ or $CF_3$; wherein $R_3$ is hydrogen, halogen, $CF_3$, aryl or heteroaryl, $NO_2$ or $OCF_3$; wherein $R_4$ is hydrogen, halogen, $CF_3$, aryl or heteroaryl, $NO_2$ or linear or branched chain alkoxy; wherein $R_6$ is hydrogen or linear or branched alkyl; wherein $R_7$ is hydrogen, cyano, hydroxyalkyl, carboxyl, halogen, hydroxyl, formyl, $NO_2$ or halogen; and wherein $R_8$ is hydroxyl or $NR_{11}R_{12}$; wherein $R_9$ and $R_{10}$ are independently hydrogen, CN or hydroxyalkyl; and wherein $R_{11}$ and $R_{12}$ are independently hydrogen, alkyl, hydroxyalkyl, arylalkyl, hydroxyarylalkyl or aryl.

In one embodiment, the present invention provides a compound as shown above wherein when XY is N=N, Z is CH and $R_2$ is hydrogen, then $R_3$ is halogen, $CF_3$ or $OCF_3$. In another embodiment, the present invention provides a compound wherein when Z is N and $R_2$ is $CF_3$, then $R_3$ is hydrogen or halogen; $R_4$ is hydrogen, halogen, alkoxy, or $CF_3$; $R_1$, $R_5$, $R_6$, $R_7$, $R_9$ and $R_{10}$ are hydrogen. The present also provides a compound as above shown wherein when XY is CH=CH, Z is CH and $R_2$ is $CF_3$, $R_7$ is hydrogen, cyano, halogen, hydroxyl, carboxyl or $B(OH)_2$. One example of an azo compound provided herein has the structure:

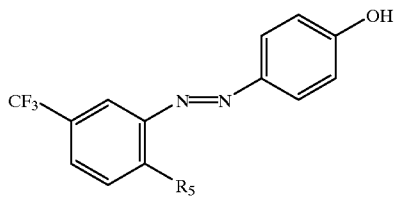

wherein $R_5$ is hydrogen or halogen. A preferred compound has the structure:

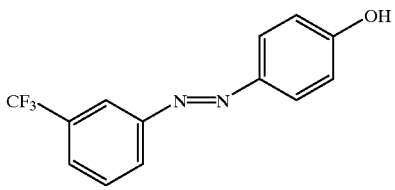

Another example of an azo compound provided by the present invention has the structure:

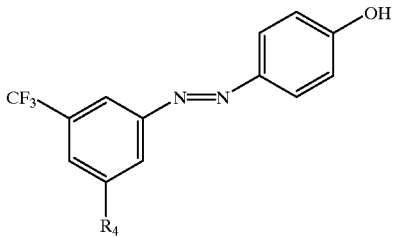

wherein $R_4$ is alkoxy or $CF_3$. In particular, the present invention provides a compound wherein $R_4$ is methoxy.

An example of the stilbene compound of the invention has the structure:

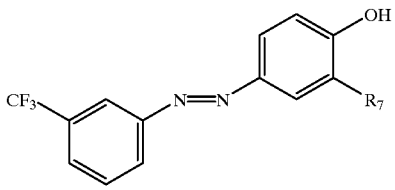

wherein $R_7$ is hydrogen, cyano, $B(OH)_2$, or halogen. In one embodiment, the compound has the structure:

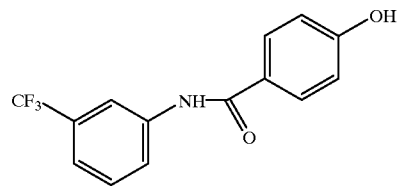

As used herein, the term "alkyl" refers to a straight or branched chain alkyl having up to about twelve carbon atoms. Typical alkyl groups include methyl, ethyl, propyl, isopropyl, butyl, sec-butyl, t-butyl, pentyl, 5-methylpentyl, hexyl, heptyl, 3,3-dimethylheptyl, octyl, decyl, undecyl, and the like. The term "halo" or "halogen" encompasses fluorine, chlorine, bromine and iodine.

The term "substituted alkyl" refers to substitution of one or more hydrogen atoms of the alkyl moiety with a substituent independently selected from halo, hydroxy, protected hydroxy, amino, protected amino, acyloxy, nitro, carboxy, protected carboxy, carbamyl, aryl, substituted aryl or alkoxy. The term "alkoxy" refers to a straight or branched chain moiety containing up to about twelve carbon atoms and at least one oxygen atom. Typical alkoxy groups include methoxy, ethyoxy, propoxy, butoxy, sec-butoxy, pentoxy, heptoxy, octyloxy, and the like.

The term "aryl" encompasses a non-heterocyclic moiety containing either a single aromatic ring or multiply fused rings wherein at least one ring is aromatic, and wherein every ring contains only carbon atoms within the ring. The term "heteroaryl" refers to a similar moiety in which there is at least one non-carbon atom within a ring thereof. Typical examples of "aryl" groups include phenyl, naphthyl, dihydronathyl, anthracenyl, indanyl, and the like. Typical examples of "heteroaryl" groups include pyrollyl, pyridyl, furyl, indolyl, benzofuranyl, benzothiophenyl, imidazolyl, and the like.

The term "substituted aryl" or "substituted heteroaryl" refers respectively to an aryl or heteroaryl group substituted with one, two or three substituents independently selected from halo, hydroxy, protected hydroxy, cyano, nitro, alkyl, alkoxy, carboxy, protected carboxy, carbamoylmethyl, hydroxymethyl, amino, aminomethyl, trifluoromethyl, N-methylsulfonylamino, and the like.

The term "hydroxy protecting group" refers to a substituent of a hydroxy group that is commonly employed to block or protect the hydroxy functionality while reactions are carried out on other functional groups on the compound. Examples of such hydroxy protecting groups include tetrahydropyranyl, 2-methoxyprop-2-yl, 1-ethoxyeth-1-yl, methoxymethyl, β-methoxyethoxymethyl, methylthiomethyl, t-butyl, t-amyl, trityl, benzyl, trimethylsilyl, and the like.

When any azo or stilbene compound or isostere thereof disclosed herein is substituted by an amino, alkyl- or aryl- or heteroaryl-amino, or dialkyl- or alkylaryl- or alkylheteroaryl-amino, or diaryl- or diheteroarylamino, an acid addition salt thereof may be formed by methods known to one of skill in the art. Such salts encompass all pharmaceutically acceptable salts, including salts prepared from a mineral acid or an organic acid. Examples of useful mineral acids for this purpose are hydrochloric acid, hydrobromic acid, hydroiodic acid, phosphoric acid, sulfuric acid, and the like. Examples of organic acids used to form addition salts include p-toluenesulfonic acid, methanesulfonic acid, oxalic acid, succinic acid, citric acid, malic acid, benzoic acid, carbonic acid, and the like.

Certain of the azo compounds disclosed herein were prepared by coupling of 30 aniline-containing compounds with 16 phenol-containing compounds under conditions suited to result in azo formation. The reaction is exemplified as follows:

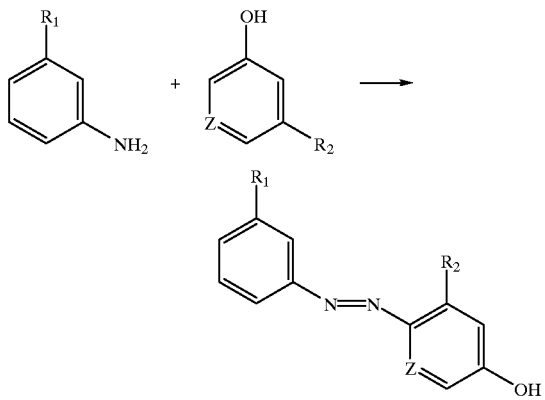

wherein Z is CH or N. The anilines used in the above-shown reaction include: 6-fluoro-3-trifluoromethylaniline, 4-fluoro-3-trifluoromethylaniline, 2-fluoro-3-trifluoromethylaniline, 3-methoxyaniline, 3-methylaniline, aniline, 3-chloroaniline, 4-trifluoromethylaniline, 2-trifluoromethylaniline, 3-trifluoromethylaniline, 3-carboxy-5methoxyaniline, 3-cyanoaniline, 4-acetylaniline, 3-acetylaniline, 2-acetylaniline, 3(hydroxymethyl)aniline, 2-(hydroxymethyl)aniline, 3-trifluoromethyl-6-methoxyaniline, 3-trifluoromethyl-5-methoxyaniline, 3,5-di(trifluoromethyl)aniline, 4-nitroaniline, 2-amino-4-nitro-pyridine, 4-aminopyridine, 4-(ethoxycarbonyl)aniline, 4-chloroaniline, 4-cyanoaniline, 3-nitroaniline, 4-trifluoromethoxyaniline, 2-anmino-6-methoxy-benozthiazole, 2'-hydroxyethyl aniline-3-sulfinate, etc.

The phenols used in the reaction include: 2-hydroxypyridine, 3-hydroxypyridine, 3-(N-acetylamino) phenol, 3-(hydroxymethyl)phenol, 3-(hydroxymethyl) phenol, 3-cyanophenol, 2-cyanophenol, phenol, 4-nitro-3-(hydroxymethyl)phenol, acetovanillone, 2-nitro-5-carboxyphenol, 4-trifluoromethylphenol, 2-hydroxynicotinic acid, 1,3-benzodioxole, 3-nitrophenol, 3-methylphenol, etc.

The novel azo and stilbene compounds and isosteres thereof disclosed herein have utility in the treatment of various fungal infections, in both humans, animals and plants. Examples of infections which may be treated include systemic fungal infections, dermatological infections and plant fungal diseases. In addition, these disclosed compounds have the additional utility of inhibiting RNA transcription, both in vivo and in vitro.

Accordingly, the present invention provides a method of inhibiting RNA transcription in a subject which comprises administering an amount of a compound having the structure:

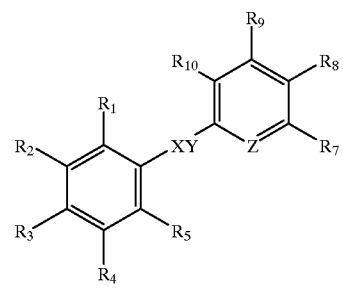

wherein XY is N=N, CH=CH, (C=O)—NH or NH—(C=O); wherein Z is $CR_6$ or N; wherein $R_1$, $R_2$ and $R_5$ are independently hydrogen, halogen, $NO_2$ or $CF_3$; wherein $R_3$ is hydrogen, halogen, $CF_3$, aryl or heteroaryl, $NO_2$ or $OCF_3$; wherein $R_4$ is hydrogen, halogen, $CF_3$, aryl or heteroaryl, $NO_2$ or linear or branched chain alkoxy; wherein $R_6$ is hydrogen or linear or branched alkyl; wherein $R_7$ is hydrogen, cyano, hydroxyalkyl, carboxyl, halogen, hydroxyl, formyl, $NO_2$ or halogen; and wherein $R_8$ is hydroxyl or $NR_{11}R_{12}$; wherein $R_9$ and $R_{10}$ are independently hydrogen, CN or hydroxyalkyl; and wherein $R_{11}$ and $R_{12}$ are independently hydrogen, alkyl, hydroxyalkyl, arylalkyl, hydroxyarylalkyl or aryl; to the subject, said amount being effective to inhibit RNA transcription.

In a certain embodiment, the present invention provides a method as described which further comprises co-administering an amount of a synergistic agent to the subject, said amount in combination with said compound being effective to inhibit RNA transcription. Specifically, the synergistic agent may be amphotericin B.

In accord with the method, in one embodiment, when Z is N and $R_2$ is $CF_3$, then $R_3$ is hydrogen or halogen; $R_4$ is hydrogen, halogen, alkoxy, or $CF_3$; $R_1$, $R_5$, $R_6$, $R_7$, $R_9$ and $R_{10}$ are hydrogen. Also, in another embodiment, when XY is N=N, Z is CH and $R_2$ is hydrogen, then $R_3$ is halogen, $CF_3$ or $OCF_3$. In another embodiment, the method may be practiced wherein when XY is CH=CH, Z is CH and $R_2$ is $CF_3$, $R_7$ is hydrogen, cyano, halogen, hydroxyl, carboxyl or $B(OH)_2$. In yet another embodiment, the method is carried out wherein the compound has the structure:

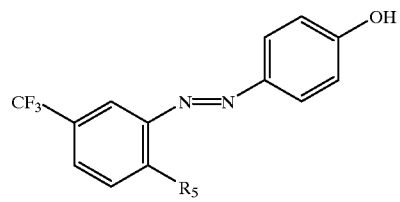

wherein $R_5$ is hydrogen or halogen.

Furthermore, the present invention provides a method of treating a subject suffering from a fungal disease which comprises administering an amount of a compound having the structure:

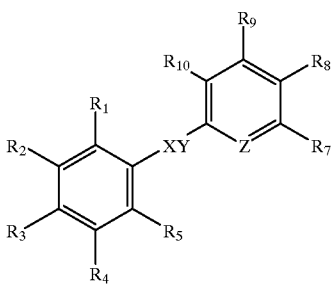

wherein XY is N=N, CH=CH, (C=O)—NH or NH—(C=O); wherein Z is $CR_6$ or N; wherein $R_1$, $R_2$ and $R_5$ are independently hydrogen, halogen, $NO_2$ or $CF_3$; wherein $R_3$ is hydrogen, halogen, $CF_3$, aryl or heteroaryl, $NO_2$ or $OCF_3$; wherein $R_4$ is hydrogen, halogen, $CF_3$, aryl or heteroaryl, $NO_2$ or linear or branched chain alkoxy; wherein $R_6$ is hydrogen or linear or branched alkyl; wherein $R_7$ is hydrogen, cyano, hydroxyalkyl, carboxyl, halogen, hydroxyl, formyl, $NO_2$ or halogen; and wherein $R_8$ is hydroxyl or $NR_{11}R_{12}$; and wherein $R_9$ and $R_{10}$ are independently hydrogen, CN or hydroxyalkyl; and wherein $R_{11}$ and $R_{12}$ are independently hydrogen, alkyl, hydroxyalkyl, arylalkyl, hydroxyarylalkyl or aryl; to the subject, said amount being effective to treat the subject.

In a certain embodiment, the method described further comprises co-administering an amount of a synergistic agent to the subject, said amount in combination with said compound being effective to treat the subject. In a particular embodiment of the method, the synergistic agent is amphotericin B.

In one embodiment, the present invention provides the method as described wherein when Z is N and $R_2$ is $CF_3$, then $R_3$ is hydrogen or halogen; $R_4$ is hydrogen, halogen, alkoxy, or $CF_3$; $R_1$, $R_5$, $R_6$, $R_7$, $R_9$ and $R_{10}$ are hydrogen. In another embodiment, when XY is N=N, Z is CH and $R_2$ is hydrogen, then $R_3$ is halogen, $CF_3$ or $OCF_3$. In yet another embodiment, when XY is CH=CH, Z is CH and $R_2$ is $CF_3$, $R_7$ is hydrogen, cyano, halogen, hydroxyl, carboxyl or $B(OH)_2$.

In one embodiment, the method as described may be practiced wherein the compound has the structure:

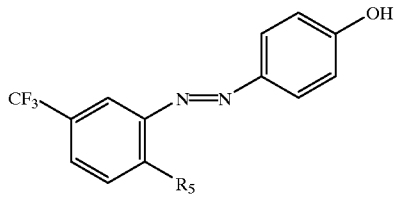

wherein $R_5$ is hydrogen or halogen.

It is within the scope of the present invention to prepare compounds identified using methods disclosed herein as RNA polymerase inhibitors which are modified to enhance potency, efficacy, uptake, stability, and suitability for use in pharmaceutical formulations, etc. These modifications are achieved and tested using methods well-known in the art.

The ability of the azo and stilbene compounds taught herein to inhibit mRNA replication in vitro, as demonstrated in the Tables below, shows that the compounds are useful to treat, prevent or ameliorate fungal infections, both in vivo and in vitro, in subjects suffering therefrom.

The magnitude of the therapeutic dose of the compounds of the invention will vary with the nature and severity of the condition to be treated and with the particular compound and its route of administration. In general, the daily dose range for antifungal activity lies in the range of 0.001 to 100 mg/kg of body weight in a mammal, preferably 0.001 to 25 mg/kg, and most preferably 0.001 to 1.0 mg/kg, in single or multiple doses. In unusual cases, it may be necessary to administer doses above 100 mg/kg.

Any suitable route of administration may be employed for providing a mammal, especially a human, with an effective dosage of a compound disclosed herein. For example, oral, rectal, topical, enteral, parenteral, ocular, pulmonary, nasal, etc., routes may be employed. Dosage forms include tablets, troches, dispersions, suspensions, solutions, capsules, creams, ointments, aerosols, etc.

The compositions include compositions suitable for oral, rectal, topical (including transdermal devices, aerosols, creams, ointments, lotions and dusting powders), parenteral (including subcutaneous, intramuscular and intravenous), ocular (ophthalmic), pulmonary (nasal or buccal inhalation) or nasal administration. Although the most suitable route in any given case will depend largely on the nature and severity of the condition being treated and on the nature of the active ingredient. They may be conveniently presented in unit dosage form and prepared by any of the methods well known in the art of pharmacy.

In preparing oral dosage forms, any of the usual pharmaceutical media may be used, such as water, glycols, oils, alcohols, flavoring agents, preservatives, coloring agents, and the like in the case of oral liquid preparations (e.g., suspensions, elixers and solutions); or carriers such as starches, sugars, microcrystalline cellulose, diluents, granulating agents, lubricants, binders, disintegrating agents, etc., in the case of oral solid preparations are preferred over liquid oral preparations such as powders, capsules and tablets. If desired, capsules may be coated by standard aqueous or non-aqueous techniques. In addition to the dosage forms described above, the compounds of the invention may be administered by controlled release means and devices.

Pharmaceutical compositions of the present invention suitable for oral administration may be prepared as discrete units such as capsules, cachets or tablets each containing a predetermined amount of the active ingredient in powder or granular form or as a solution or suspension in an aqueous or nonaqueous liquid or in an oil-in-water or water-in-oil emulsion. Such compositions may be prepared by any of the methods known in the art of pharmacy. In general, compositions are prepared by uniformly and intimately admixing the active ingredient with liquid carriers, finely divided solid carriers, or both and then, if necessary, shaping the product into the desired form. For example, a tablet may be prepared by compression or molding, optionally with one or more accessory ingredients. Compressed tablets may be prepared by compressing in a suitable machine the active ingredient in a free-flowing form such as powder or granule optionally mixed with a binder, lubricant, inert diluent or surface active or dispersing agent. Molded tablets may be made by molding in a suitable machine, a mixture of the powdered compound moistened with an inert liquid diluent.

The compounds of the present invention are also useful as fungicidal agents and fungistatic agents in various agricultural applications. For example, the compounds can be used to destroy fungal infestations or curtail further fungal growth in plants.

The compounds may be used directly for fungicidal purposes but are more conveniently formulated into compositions using a carrier or diluent. The invention thus provides a fungicidal composition comprising a compound of the present invention as hereinabove defined, and a fungicidally acceptable carrier or diluent.

The invention also provides a method of combating fungi, which comprises applying to a plant, to a seed of a plant, or to the locus of the plant or seed, a compound as defined above, or a composition containing the same.

The compounds, can be applied in a number of ways. For example they can be applied, formulated or unformulated, directly to the foliage of a plant, to seeds or to other medium in which plants are growing or are to be planted. They can be sprayed on, dusted on or applied as a cream or paste formulation; or they can be applied as a vapor or controlled-release granules. Application can be to any part of the plant including the foliage, stems, branches or roots, or to soil surrounding the roots, or to the seed before it is planted; or to the soil generally, or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example fillers such as kaolin, bentonite, kieselguhr, dolomite, calcium carbonate, talc, powdered magnesia, Fuller's earth, gypsum, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example a mineral oil) for assisting the adhesion of the composition to the seed; alternatively the active ingredient can be formulated for seed dressing purposes using an organic solvent (for example N-methylpyrrolidone, propylene glycol or dimethylformamide). The compositions may also be in the form of wettable powders or water dispersible granules comprising wetting or dispersing agents to facilitate their dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent and including a suspending agent to stop the solid settling.

Compositions to be used as sprays may be in the form of aerosols wherein the formulation is held in a container under pressure in the presence of a propellant, e.g., fluorotrichloromethane or dichlorodifluoromethane.

The invention compounds can be mixed in the dry state with a pyrotechnic mixture to form a composition suitable for generating in enclosed spaces a smoke containing the compounds. Alternatively, the compounds may be used in a microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilizers (e.g., nitrogen-, potassium- or phosphorus-containing fertilisers). Compositions comprising only granules of fertilizer incorporating, for example, coated with the compound are preferred. Such granules suitably contain up to 25% by weight of the compound. The invention therefore also provides a fertilizer composition comprising a fertilizer and the compound of the invention.

Wettable powders, emulsifiable concentrates and suspension concentrates will normally contain surfactants, e.g., a wetting agent, dispersing agent, emulsifying agent or suspending agent. These agents can be cationic, anionic or non-ionic agents. Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, typically 10–85%, and preferably 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g., compounds having similar or complementary fungicidal activity or which possess plant growth regulating, herbicidal or insecticidal activity. The other fungicide can have a synergistic effect on the fungicidal activity of the compound of the invention. Examples of fungicidal compounds which may be included in the composition of the invention are carbendazim, benomyl, thiophanate-methyl, thiabendazole, fuberidazole, etridazole, dichlofluanid, cymoxanil, oxadixyl, ofurace, metalaxyl, furalaxyl, 4-chloro-N-(cyanoethoxymethyl)

benzamide, benalaxyl, fosetylaluminium, fenarimol, iprodione, prothiocarb, procymidone, vinclozolin, penconazole, myclobutanil, propamocarb, diconazole, pyrazophos, ethirimol, ditalimfos, tridemorph, triforine, nuarimol, triazbutyl, guazatine, triacetate salt of 1,1'-iminodi (octamethylene)diguanidine, buthiobate, propiconazole, prochloraz, carboxin, oxycarboxin, methfuroxam, dodemorph, BAS 454, blasticidin S, Kasugamycin, edifenphos, kitazin P, cycloheximide, phthalide, probenazole, dithianon, fentin hydroxide, fentin acetate, tecnazene, quintozene, dichloran, copper containing compounds such as copper oxychloride, copper sulphate and Bordeaux mixture, and organomercury compounds. The compounds of the invention can be mixed with soil, peat or other rooting media for the protection of plants against seed-borne, soil-borne or foliar fungal diseases.

Suitable insecticides which may be incorporated in the composition of the invention include pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, monocrotophas, buprofezin, ethroproxyfen and cycloprothrin.

Plant growth regulating compounds are compounds which control weeds or seedhead formation, or selectively control the growth of less desirable plants (e.g., grasses). Examples of suitable plant growth regulating compounds for use with the invention compounds are the gibberellins (e.g., $GA_3$, $GA_4$ or $GA_7$), the auxins (e.g., indoleacetic acid, indolebutyric acid, naphthoxyacetic acid or naphthylacetic acid), the cytokinins (e.g., kinetin, diphenylurea, benzimidazole, benzyladenine or benzylaminopurine), and the like.

The present invention will be better understood from the Experimental Details which follow. However, one skilled in the art will readily appreciate that the specific methods and results discussed are merely illustrative of the invention as described in the claims which follow thereafter.

EXAMPLE 1

Combinatorial Method

A combinatorial approach was used to synthesize azo compounds in 96-well plates. In total, six plates with 80 compounds per plate (with a total of 480 compounds) were prepared. Proton NMR studies demonstrated that about 60% of the compounds were made successfully.

General Procedure for Azo Coupling.

200 µL (0.001 mmol) of a 0.05 mM aniline solution in 1N HCl (or HOAc for water-insoluble anilines) was distributed to each well in a 96-well plate. 50 µL (0.001 mmol) of a 0.20 mM $NaNO_2$ solution in water was added once to the aniline wells at 0° C. The diazotization reaction was continued for 10 to 60 mins. The diazonium salts from step 2 were transferred to a "phenol plate" containing 200 µL (0.001 mmol) of a 0.05 mM phenol in saturated NaOAc at 0° C. The plate was then placed on a shaker for 2 hrs at room temperature, and allowed to stand overnight. The plate was centrifuged at 2000 rpm for 20 mins. Supernatants were removed from each well. 300 µL water was added to the well. The plate was shaken for 5 mins, centrifuged again at 2000 rpm for 20 mins. Supernatants were removed from each well, and the plates were dried in vacuo.

Azo Compound 1 from 3-Trifluoromethylaniline and Phenol). 200 µL (0.001 mmol) of a 0.05 mM 3-trifluoromethylaniline solution in 1N HCl was reacted with 50 µL (0.001 mmol) of a 0.20 mM $NaNO_2$ solution in water at 0° C. The diazotization reaction was continued for 10 to 60 mins. The diazonium salt generated was transferred to the "phenol plate" containing 200 µL (0.001 mmol) of 0.05 mM phenol in saturated NaOAc at 0° C. The plate was then placed on a shaker for 2 hrs at room temperature, and allowed to stand overnight. The plate was centrifuged at 2000 rpm for 20 mins. Supernatants were removed, and 300 µL water was added to the well. The plate was shaken for 5 mins, centrifuged again at 2000 rpm for 20 mins. Supernatants were removed, and the plate were dried in vacuo. The resulting azo Compound 1 was sufficiently pure for bioanalytical determinations.

EXAMPLE 2

High Throughput Screens For Inhibitors of *C. albicans* RNA Polymerase

High-throughput screens for anti-fungal agents may be performed using an in vitro format. The ability of test compounds to inhibit *C. albicans* RNA polymerase-driven transcription is tested.

The following procedure is used for cell-free high-throughput screening. A Tomtec Quadra 96-well pipetting station is used to add the reaction components to polypropylene 96-well dishes. 5 µl aliquots of test compounds dissolved in DMSO (or DMSO alone as a control) are added to wells. This is followed by 20 µl of the RNA polymerase II mixture, which consists of: 10 mM DTT, 200 mM KCl, 10 mM $Mn^{+2}$, 1.5 µM bovine serum albumin, and 0.25 µg reconstituted RNA polymerase. After allowing the test compound to interact with the RNA polymerase, 25 µl of the DNA/NTP mixture is added, containing: 1 µg calf thymus DNA, 4 µM [α-$^{32}$P]-UTP, and 400 µM each CTP, ATP, and GTP.

After incubation for 60 min at 30 C, the reaction is stopped by addition of 50 µl 15% trichloroacetic acid (TCA). The TCA-precipitated RNA is adsorbed onto double-thick glass fiber filtermats using a Tomtec cell harvester. The wells of the microtiter plate and the filter are washed twice with 5% TCA and bound radioactivity is determined using a Wallac microbeta 1450 scintillation counter.

Inhibitory activity due to the test compound is calculated according to the formula:

$$\% \text{ inhibition} = \frac{(cpm_{positive\ control} - cpm_{sample})}{cpm_{positive\ control}} \times 100$$

where $cpm_{positive\ control}$ represents the average of the cpm in wells that received DMSO alone, and $cpm_{sample}$ represents the cpm in the well that received test compound. Compounds that cause at least 50% inhibition are scored as positive "hits" in this assay.

As an additional control, EDTA is used at a concentration of 10 µM, which results in a ≧90% inhibition of transcription in this assay.

EXAMPLE 3

Biological Evaluation

Figure 4A:
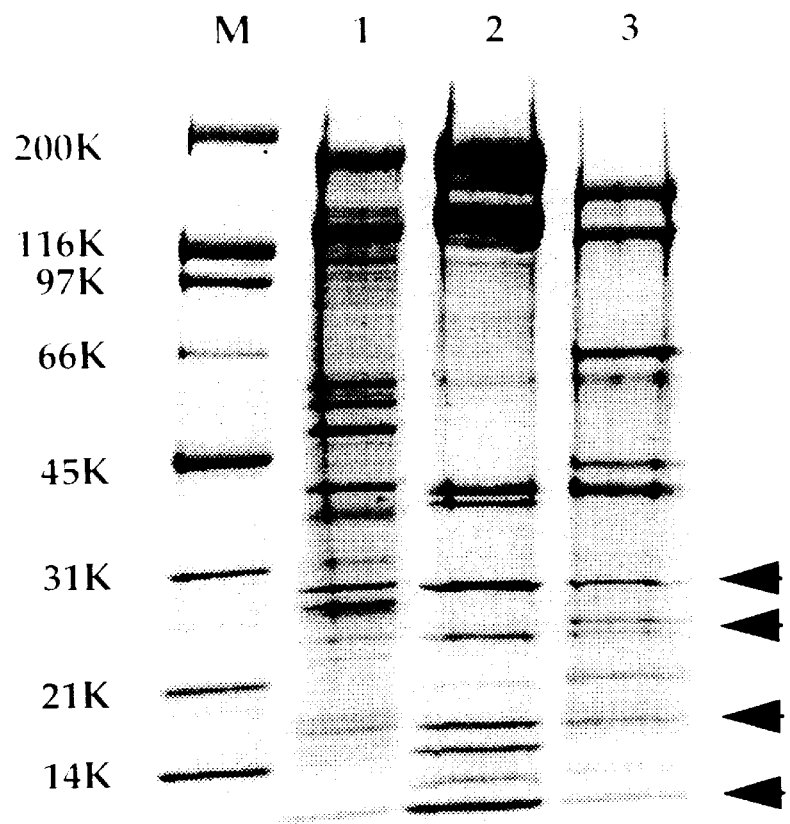
FIGS. 4A–4D illustrate fungal and human nuclear RNA polymerases.
Figure 4D:
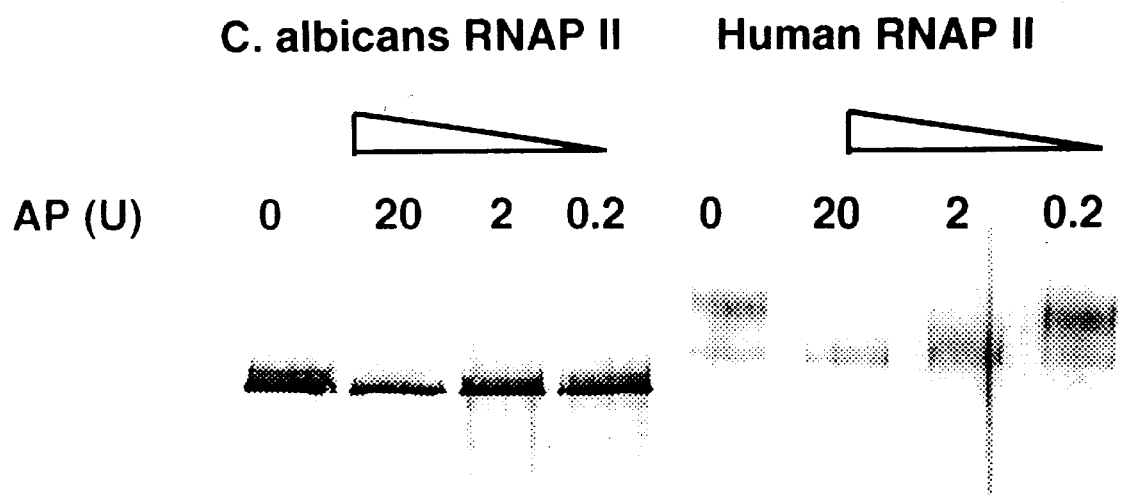
Figure 4B:
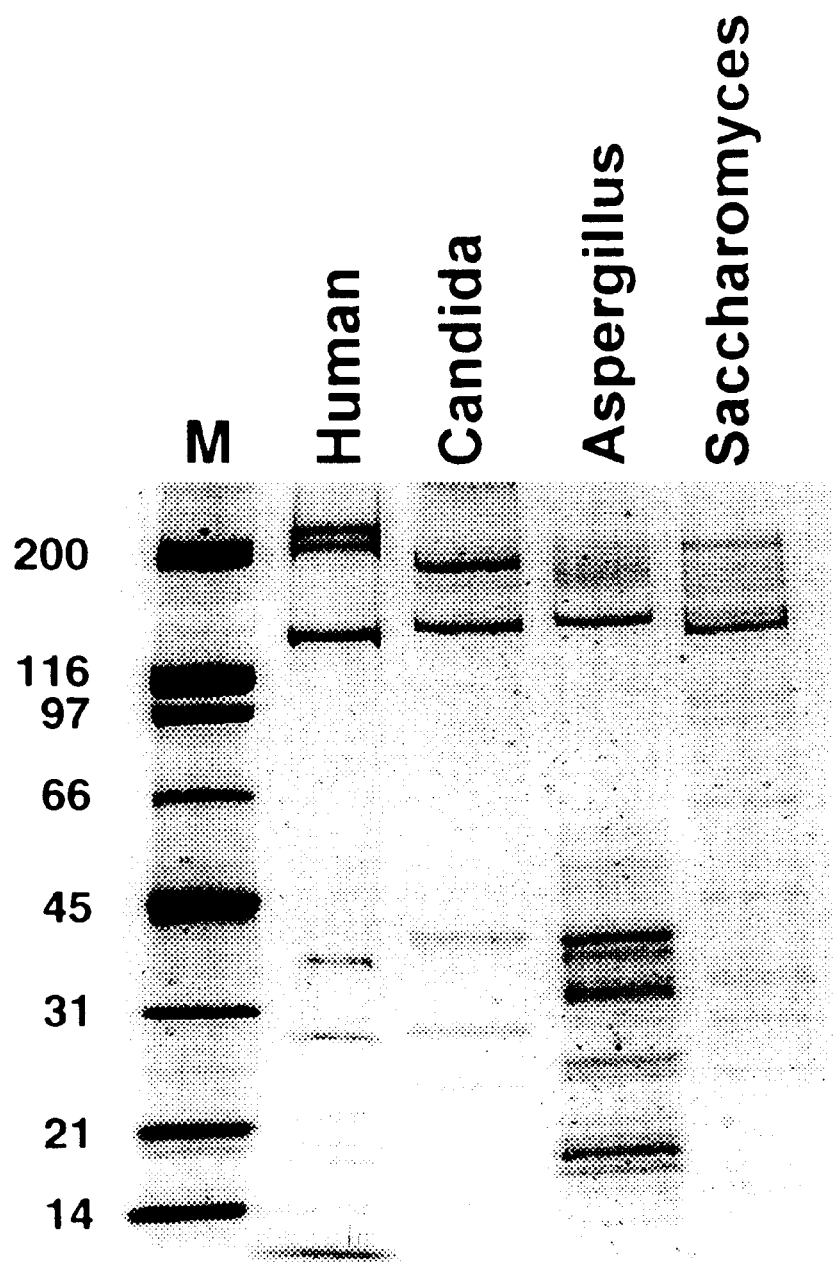
Figure 4C:
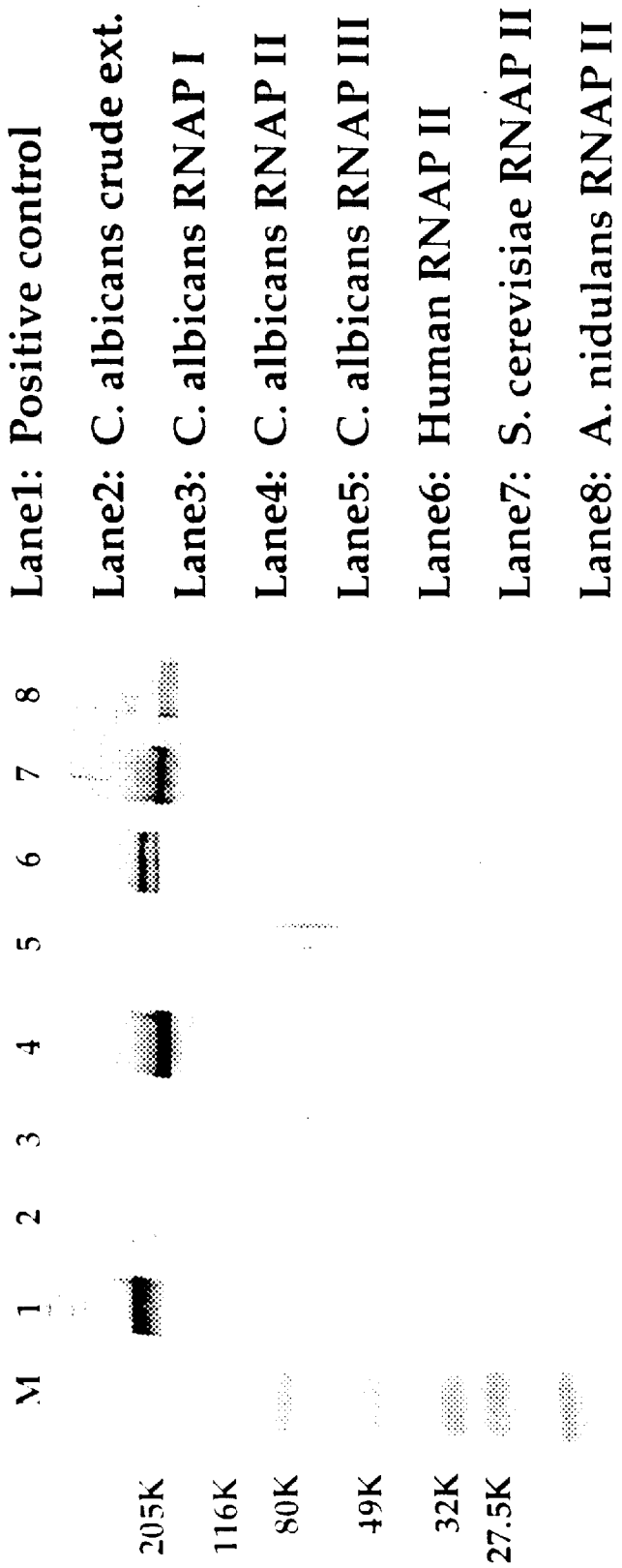

DNA-directed RNA polymerase II from *Candida albicans* was purified in sufficient quantity to support high throughput screening of large synthetic chemical and natural product libraries. A biochemical mechanism-based screen for detecting inhibitors of Pol II was developed and implemented. The screen is outlined in FIGS. 4A and 4B. Results of the screening of an azo library are presented in Table 3.

Figure 5:
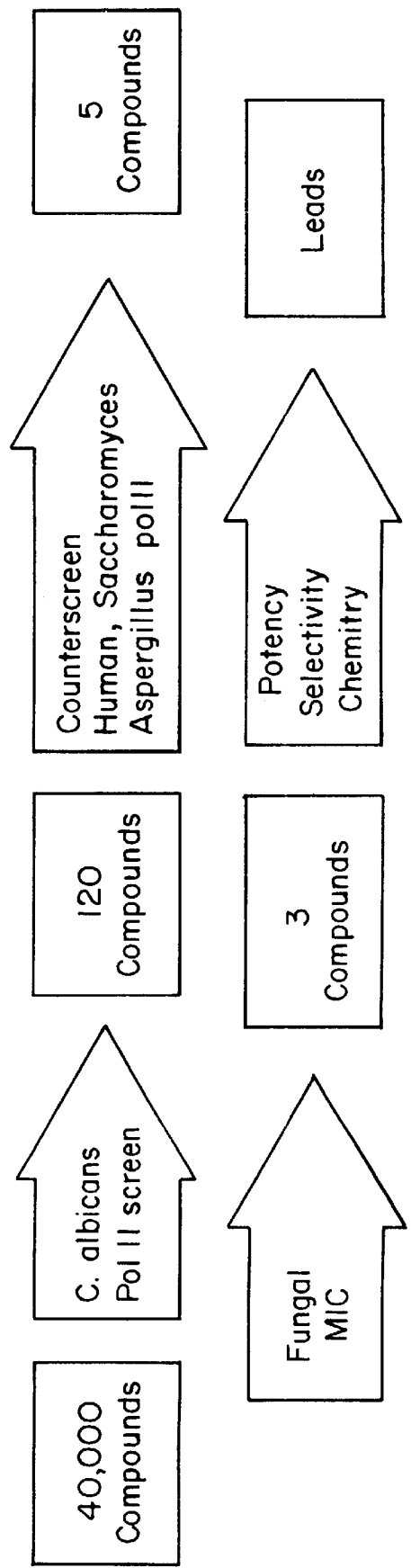
FIG. 5 illustrates the high throughput screening results.
Figure 2:
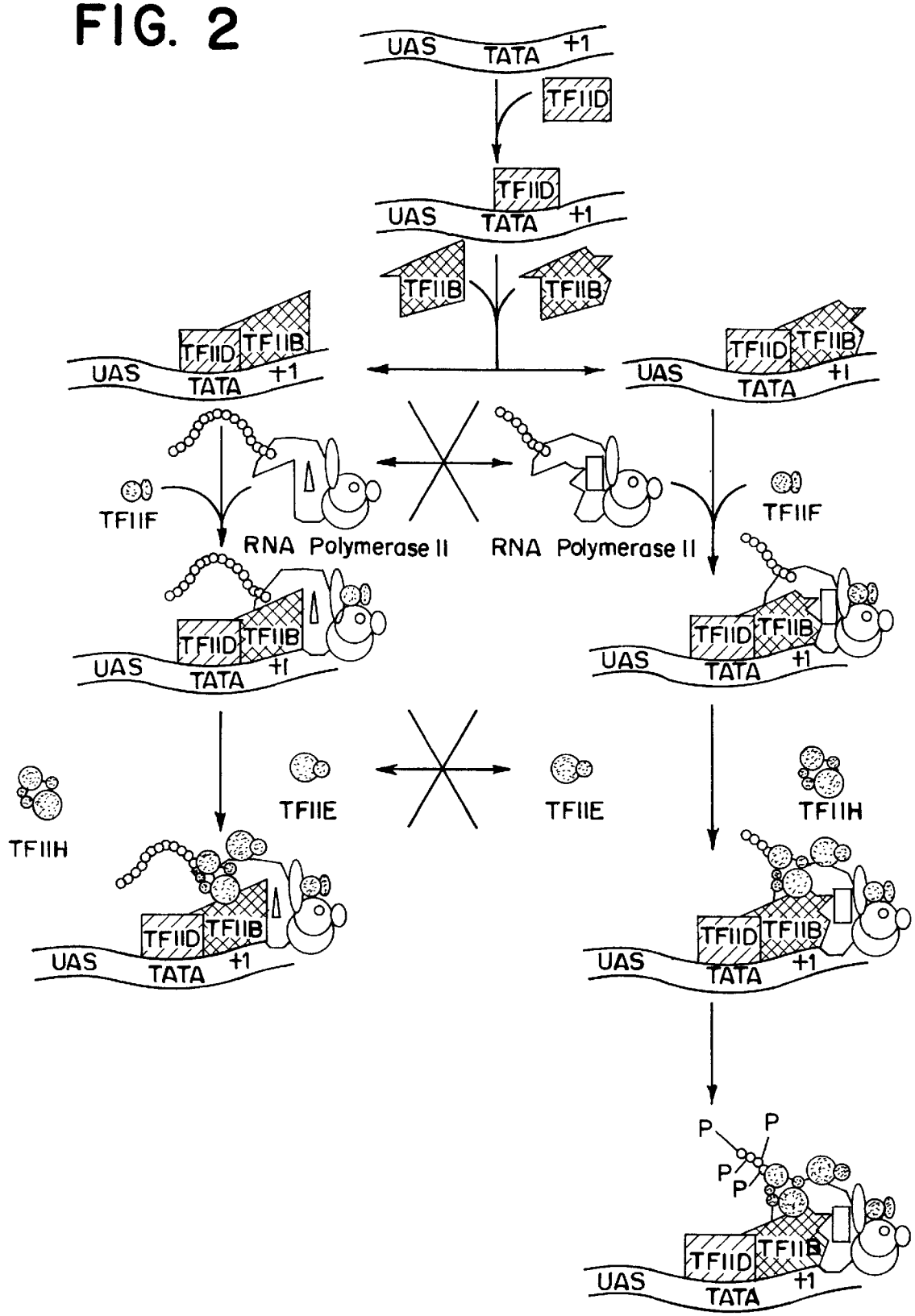
FIG. 2 illustrates the differences between the first steps of human and yeast transcription initiation.
Figure 3:
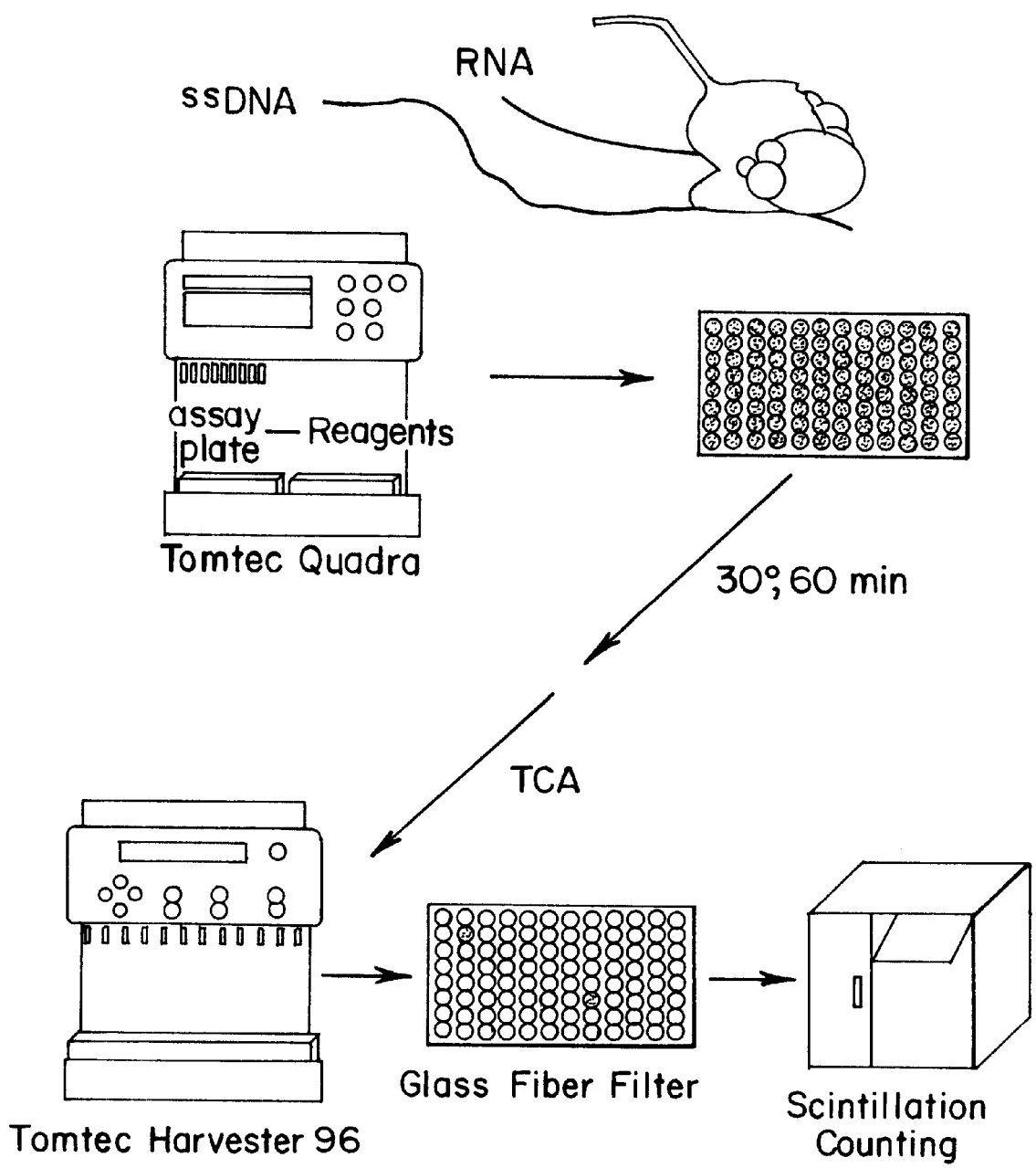
FIG. 3 illustrates the RNA polymerase elongation screen used to screen compounds for activity as RNA transcription inhibitor.

Pol II was isolated from *Aspergillus nidulans*, *Saccharomyces cerevisiae*, and human cells (FIG. 5) and used in secondary screens for fungal spectrum and specificity. Pol I and Pol III were isolated from *Candida albicans* and used as an additional mechanism to study specificity. Confirmed hits form the primary assay and were evaluated against this panel of polymerases. Agents with activity against Pol II from multiple fungal enzymes but not against the human counterpart were evaluated in vitro against fungal pathogens. The progression of compounds through the early stages of lead discovery is shown in FIG. 6.

The most potent and selective fungal Pol II inhibitors (FIG. 7) include a range of chemical types. All show potent activity against Candida, Aspergillus and Saccharomyces Pol II. Compound 1 and Compound 2 were among those selected for further characterization and development.

Compound 1

(4-[-2-[3-(trifluoromethyl)phenyl]diazenyl]phenol).

Figure 7:
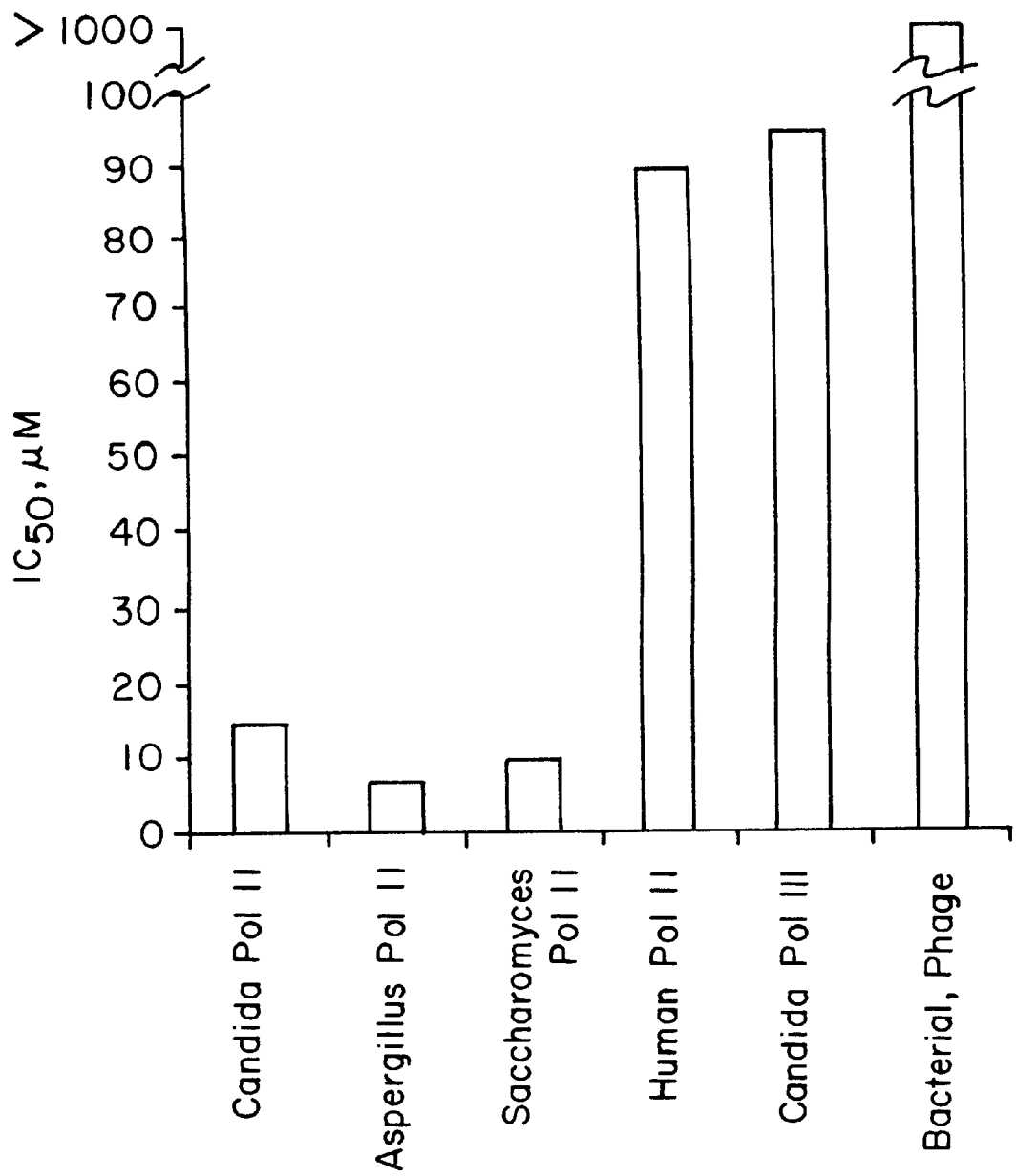
FIG. 7 illustrates polymerase inhibitor activity and broad spectrum antifungal activity for Compound 1.

Compound 1 shows potent activity as an antifungal DNA-directed RNA Pol II inhibitor (FIG. 7). This compound is selective by a factor of about 10 as compared to human Pol II, and has broad spectrum in vitro activity against yeast and filamentous fungi of medical importance (FIG. 8). Compound 1 retains antifungal activity against Candida strains resistance to ketoconazole or to amphotericin B. The compound is also active against the plant pathogen *Fusarium culmorum* with an MIC of 6.25 µg/ml, active against the human dermatophytic fungi *Trichophyton mentagrophytes* and is essentially non-toxic against monkey kidney cells. Expanded fungal panel testing is scheduled for completion in the near future.

Figure 9:
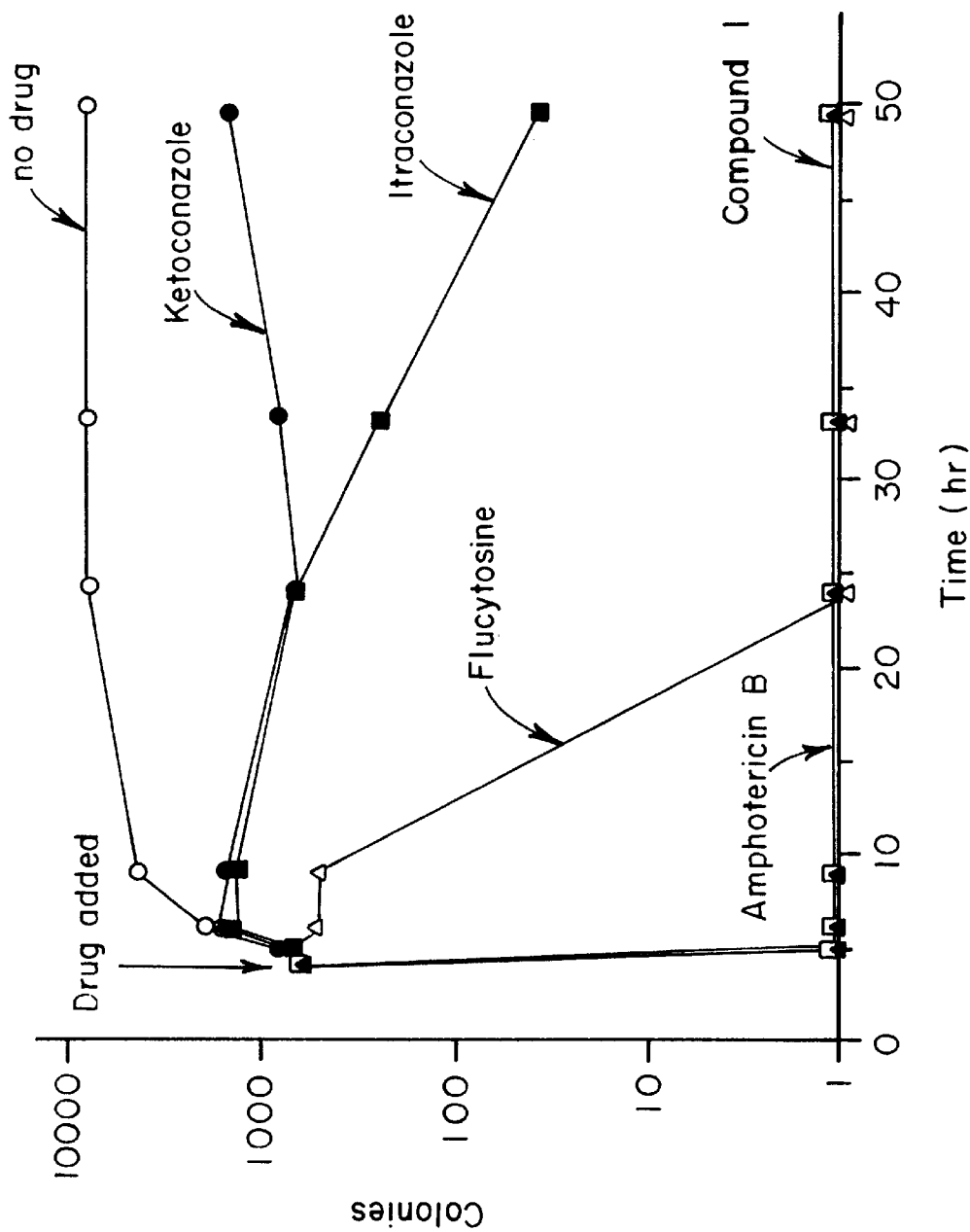
FIG. 9 illustrates the time course of fungicidal activity of Compound 1 and various other compounds.

Compound 1 is rapidly fungicidal. Exposing about $10^6$ *C. albicans* or *S. cerevisiae* cells to 25 µg/ml Compound 1 for 45 minutes leaves no detectable colony forming units (FIG. 9). Similarly, no colony forming units are detected after cells are exposed to 1.5 µg/ml of amphotericin B for a similar time. If cells are exposed to Compound 1 for 5 minutes only no CFUs are recoverable, while amphotericin B requires nearly 30 minutes to demonstrate an equivalent effect.

Figure 10:
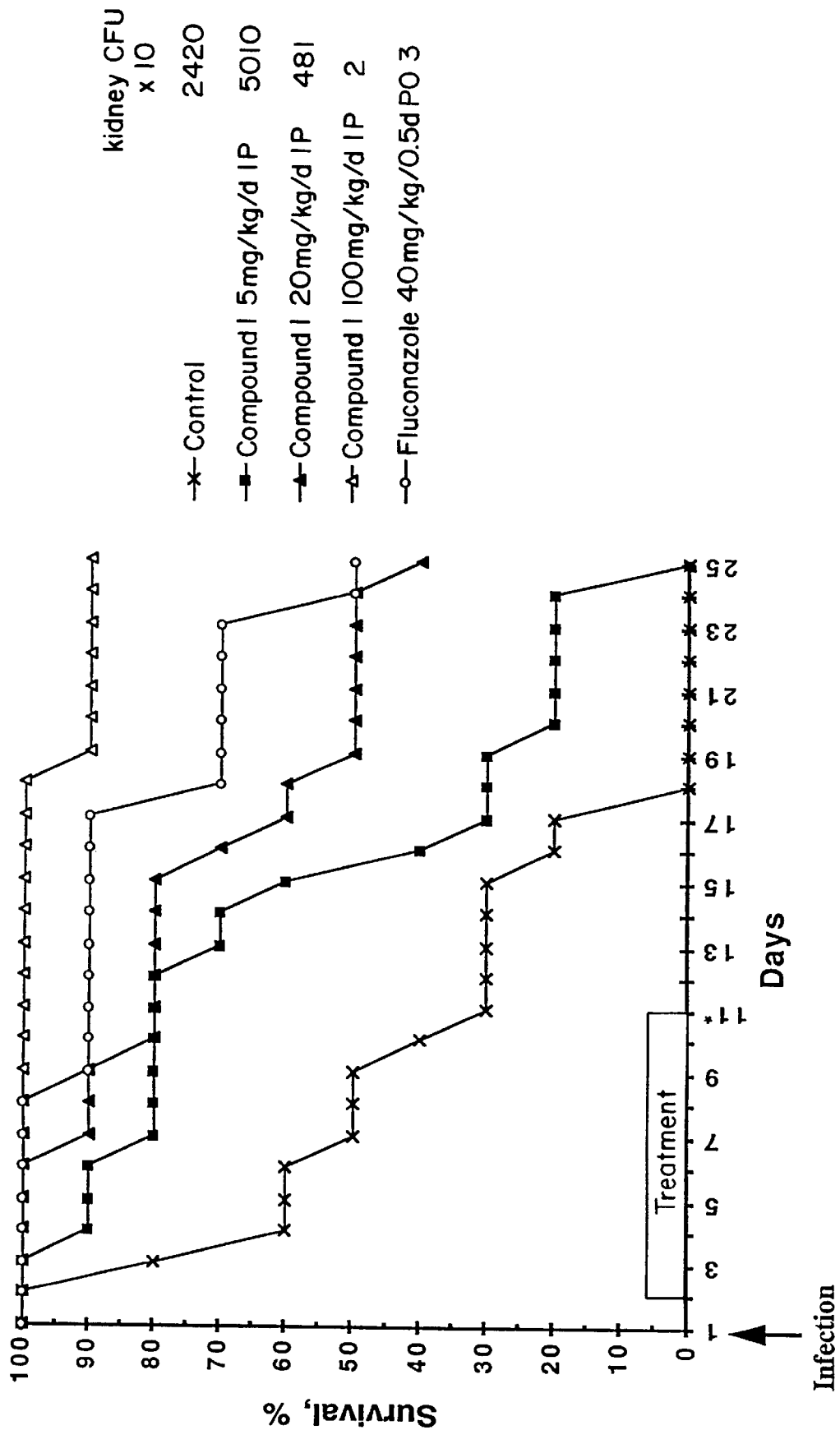
FIG. 10 illustrates IP efficacy of Compound 1 and oral efficacy of fluconazole in treatment of mouse systemic candidiasis.
Figure 11:
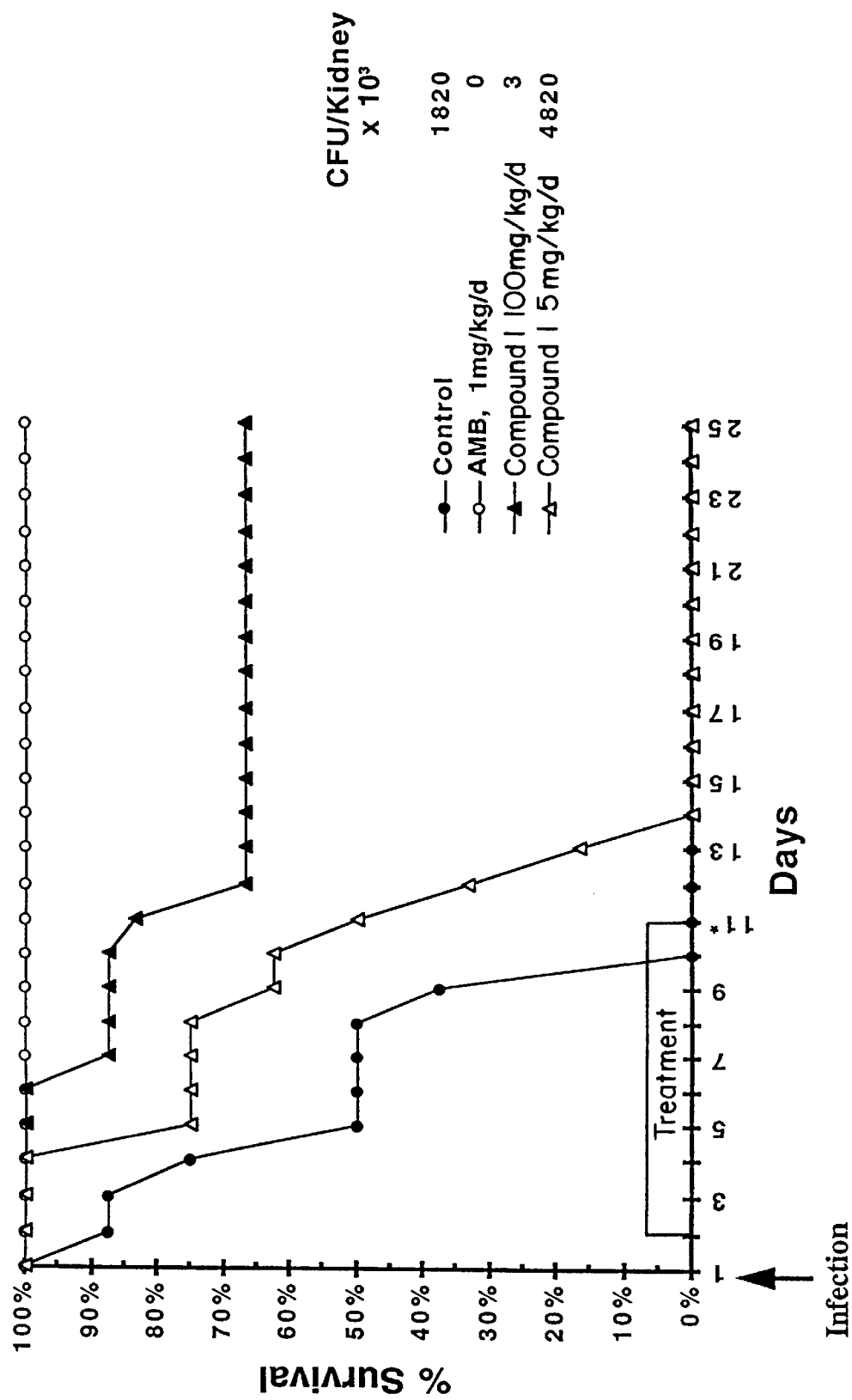
FIG. 11 illustrates IP efficacy of Compound 1 and amphotericin B (AmB) in treatment of mouse systemic candidiasis.
Figure 12:
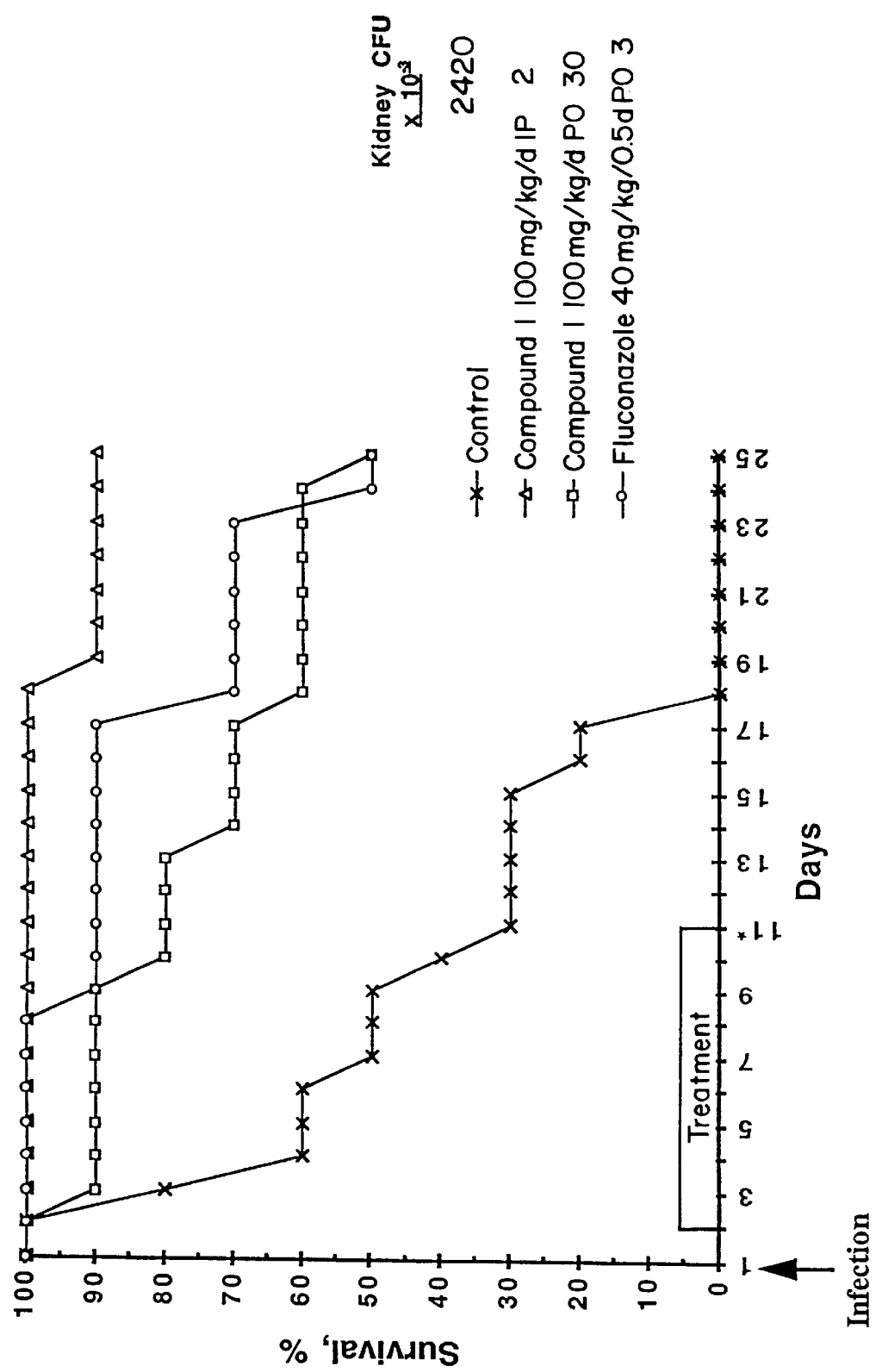
FIG. 12 illustrates oral efficacy of compound 1 and fluconazole in treatment of mouse candidiasis.
Figure 13:
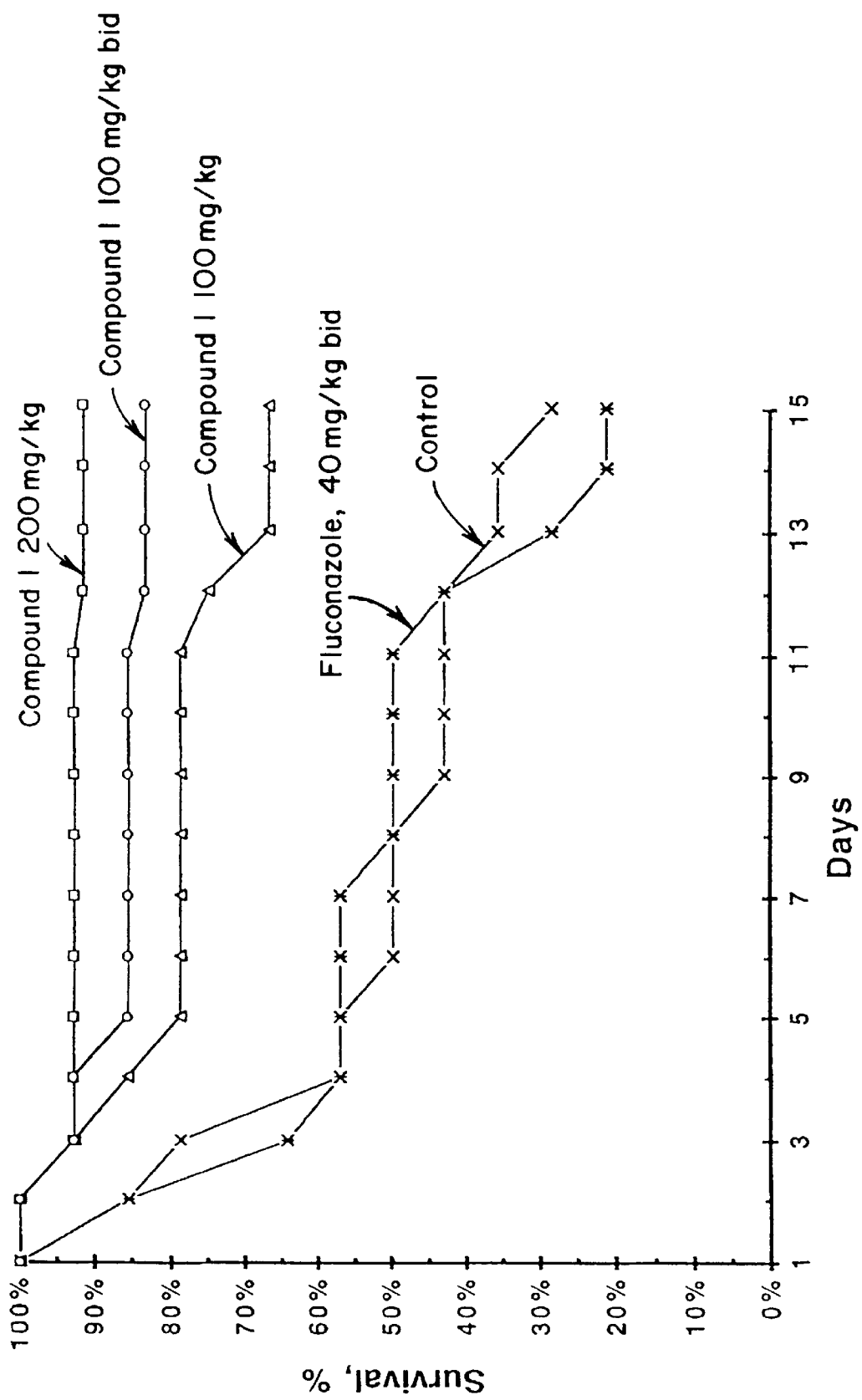
FIG. 13 illustrates the activity of Compound 1 against fluconozole-resistant candidiasis.

In addition, Compound 1 was efficacious in a murine model for systemic candidiasis (FIG. 10). It prolonged mean and median survival times of treated mice in the dosage range of 5 mg/kg/d to 100 mg/kg/d on aq.d., d2–11 schedule. Compound 1 administered IP at 20 mg/kg/d produced a similar survival pattern as that produced by the positive control compound fluconazole administered orally at 40 mg/kg/b.i.d. Both Compound 1 and fluconazole reduced recoverable colonies from the kidneys of treated animals. The efficacy of Compound 1 was confirmed in a separate experiment using amphotericin as a control (FIG. 11). Compound 1 was also efficacious when administered orally to mice with an established systemic Candida infection (FIG. 12). The compound given orally at 100 mg/kg/d was similar in efficacy to fluconazole at 40 mg/kg/b.i.d. as measured by survival time, per cent cures and kidney burden. No signs of compound related toxicity were noted in animals treated IP or PO with Compound 1 for 10 days at 100 mg/kg/d. Compound 1 is also effective against systemic candidiasis caused by a strain of *C. albicans* resistant to fluconazole (FIG. 13). Additional animal testing will include acute toxicity determination, route and schedule dependency in standard efficacy models, efficacy testing in immunosuppressed Candida infected mice, efficacy in an Aspergillus infection model, and pharmacokinetics following IV and oral dosing.

A frequency of resistance study is conducted for Compound 1 using *C. albicans* and *S. cerevisiae*, with amphotericin B as the comparator. Selective concentrations of each compound between 1× and 10× the MIC are used for each compound. Results indicate that the frequency of resistance is $<1\times10^{-8}$ in *C. albicans* and about $1–5\times10^{-8}$ in *S. cerevisiae*.

A safety assessment of Compound 1 was conducted. The compound was negative for effects in a number of CNS, cardiovascular, intermediary metabolism, allergy/inflammation and gastrointestinal targets. The compound was nontoxic when administered orally at 300 mg/kg.

Figure 14:
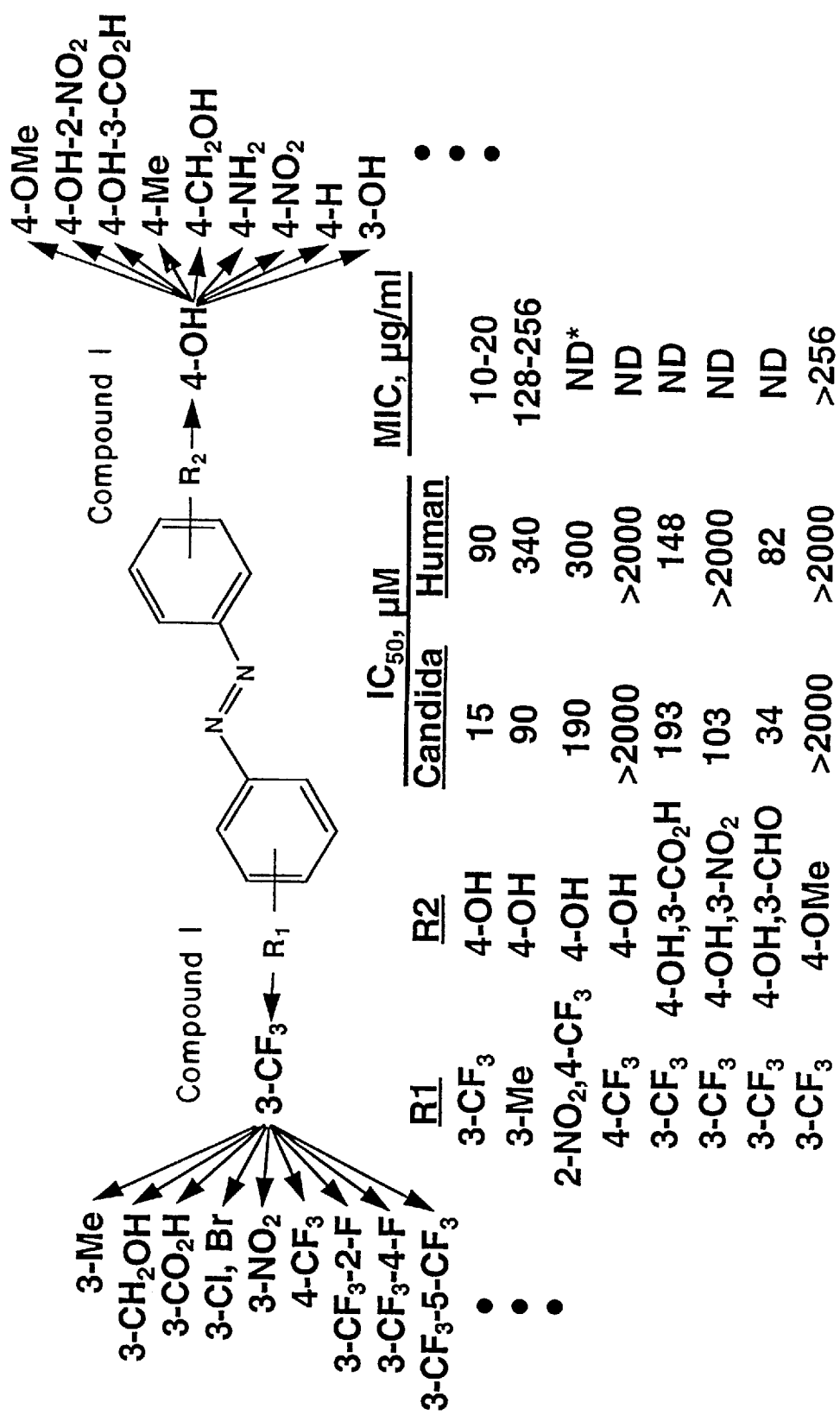
FIG. 14 illustrates inhibition data for azo analogues with varying pendant groups.
Figure 16:
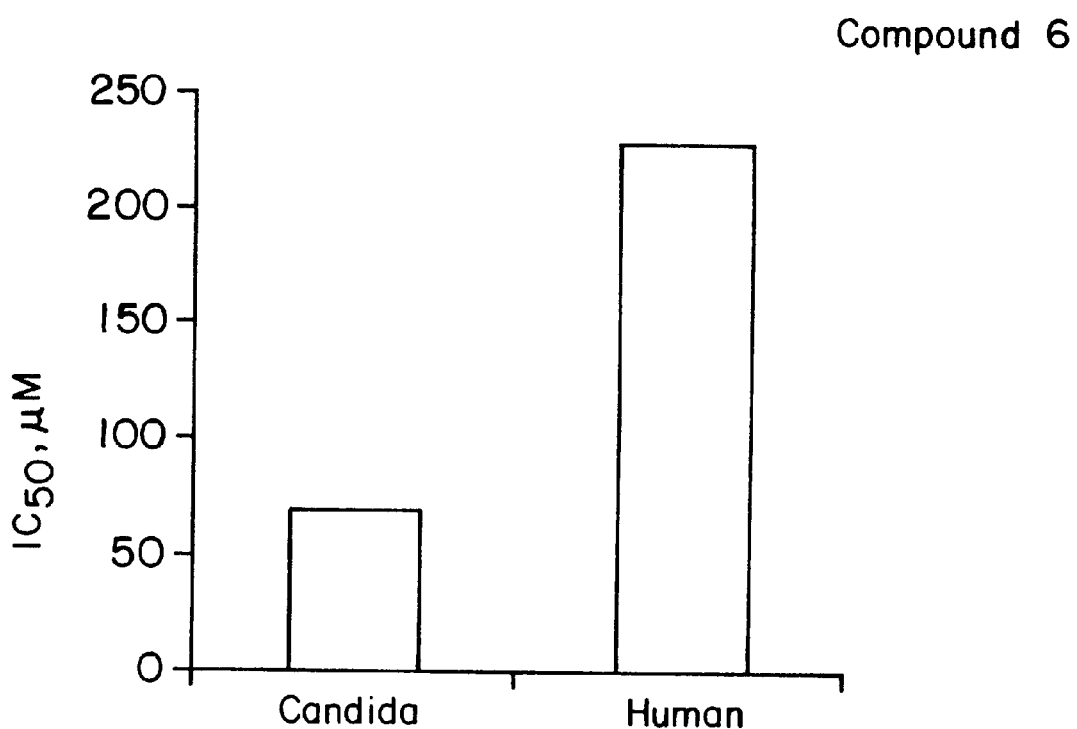
FIG. 16 illustrates enzyme inhibition and antifungal activity for Compound 6.

In an analogue development program intended to develop a structure-activity relationship (SAR) for enzymatic selectivity, enzymatic potency and antifungal potency, a combinatorial synthesis approach was undertaken to rapidly define the SAR for this series of compounds and to rapidly identify superior analogs. An initial synthesis of 480 compounds focused on modifications of both the pendant groups and the azo linkage. Modification of the pendent groups on Compound 1 (FIG. 13) strongly suggest that the 4-OH group at the $R_2$ position is required for Pol II inhibitory activity. Several isosteric replacements were made for the azo group (Table 1; FIG. 14). Initial studies indicated that the stilbene isostere of Compound 1 retained selective activity against Candida Pol II with respect to human Pol II and had antifungal activity (FIGS. 16 and 17). The stilbene analog, Compound 6, has been characterized in vitro and in vivo. Human and candida Pol II activity for a series of substitution variants of compound 1 is shown in Table 2.

Compound 6

(4-2-[3-trifluoromethyl)phenyl]ethenyl]phenol

Figure 15:
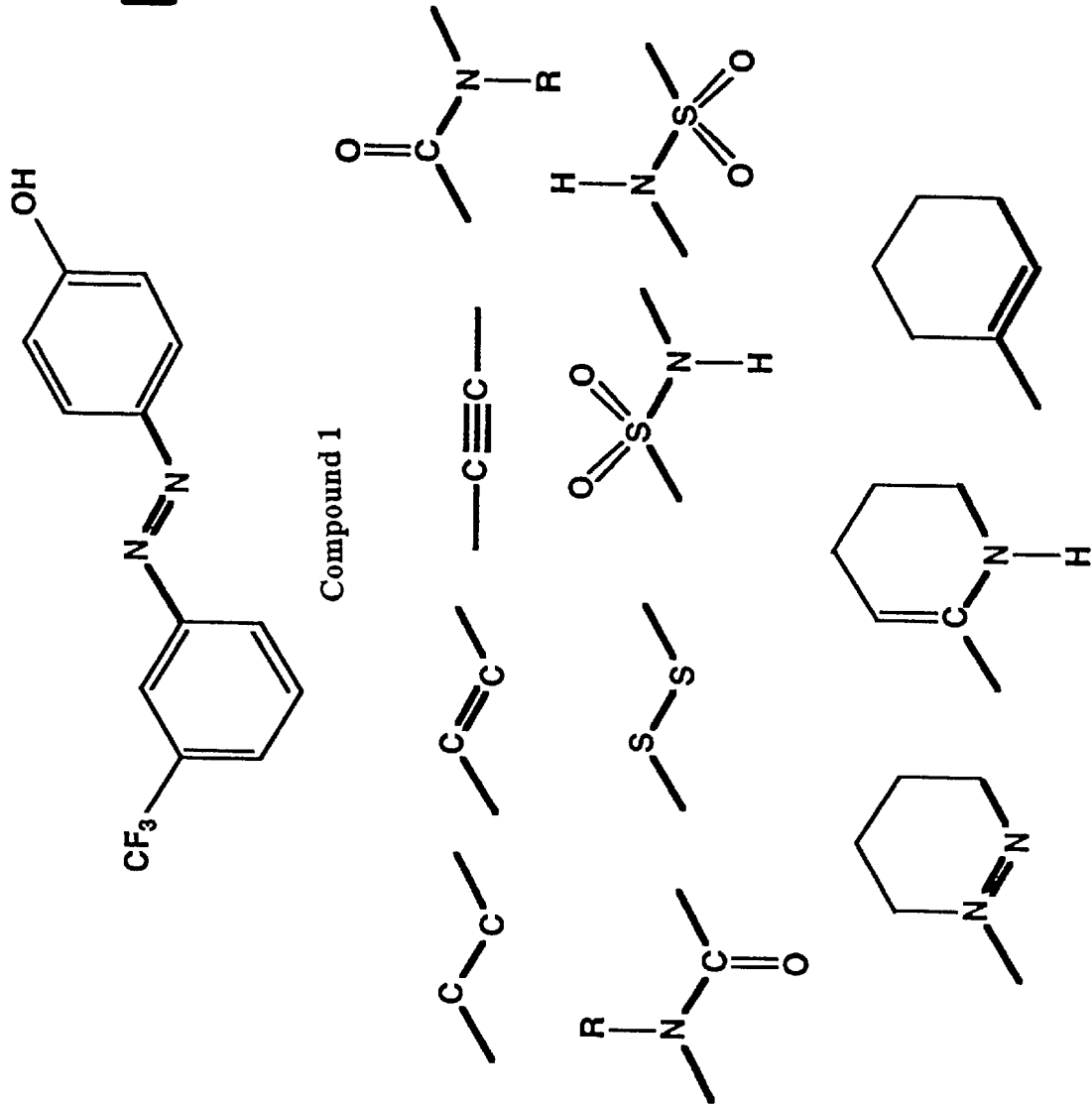
FIG. 15 illustrates replacement of the azo linkage in Compound 1.

The ability of Compound 6 to inhibit fungal RNA Pol II activity and microbial growth is shown in FIGS. 15 and 17. The data suggest that the compound is broadly active against fungi and is selective relative to inhibition of human Pol II.

Figure 18:
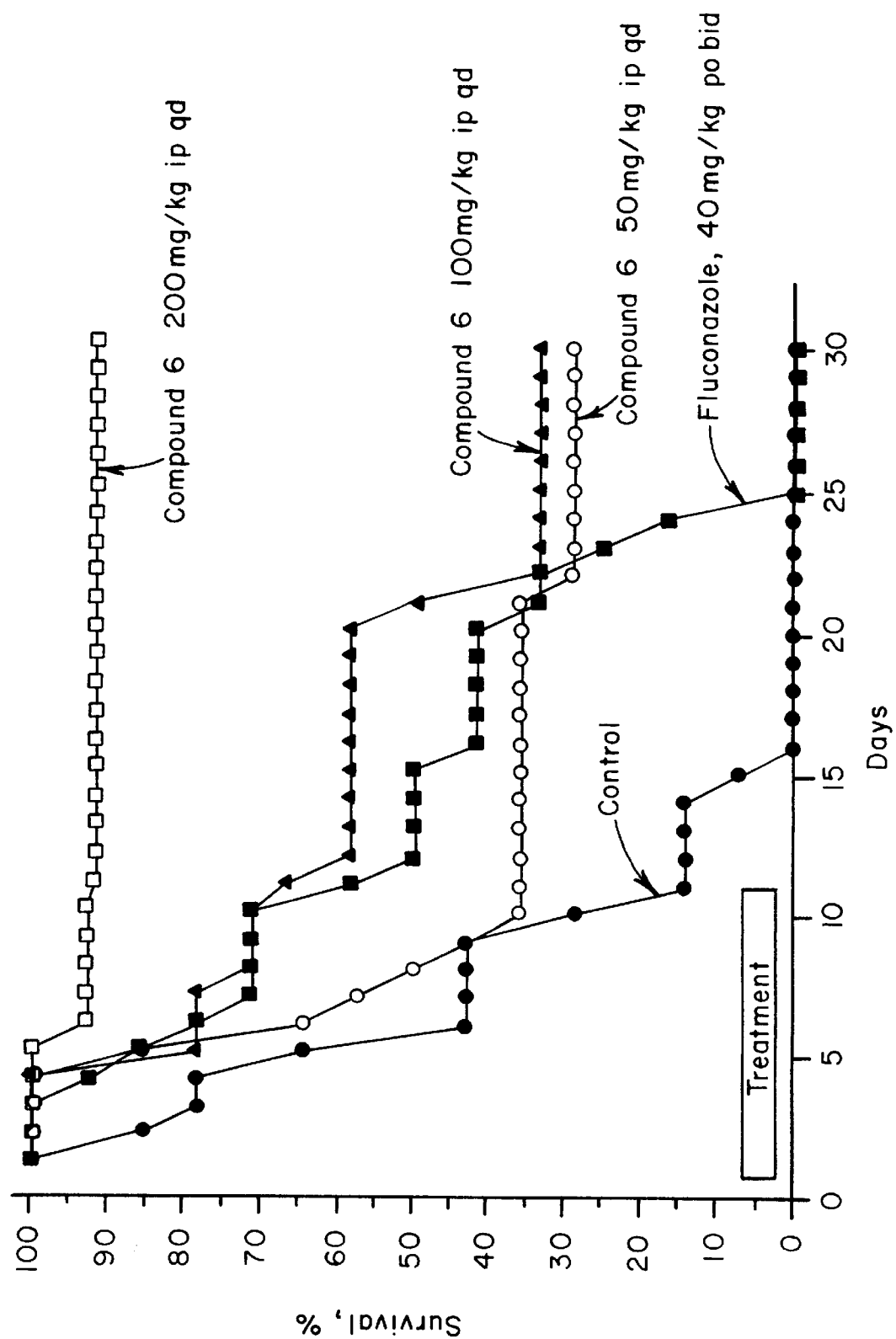
FIG. 18 illustrates the activity of Compound 6 against mouse systemic candidiasis.

Compound 6 was evaluated for antifungal efficacy in a systemic candidiasis model in immunocompetent mice (FIG. 18). The compound was administered IP on a q.d., d2–11 schedule. There was no evidence of compound-related toxicity in any of the treatment groups. 90% long term survival was seen formice treated with Compound 6 at 200/mg/kg. 30% of mice survived when treated with Compound 6 at 100 mg/kg/d. Compound 6 was also effective against systemic candidiasis when administered orally (FIG. 19) and it was effective in treating infections caused by fluconazole-resistant *C. albicans*.

Compound 2

(4-(E)-2-[6-bromo-2,4-dintro)phenyl]diazenyl]-(2-methyl-4-(N,N-n-butyl-2-hydroxyethyl)-amino)

Compound 2 was identified in the primary high throughput elongation screen as a potent inhibitor of fungal Pol II (FIG. 7). It has some structural similarity to Compound 1 but does not appear to be fungicidal and has relatively low potency against *Candida albicans* in vitro. Compound 2 does appear, however, to act synergistically with amphotericin B. Sub-MIC levels of amphotericin B (⅓ of the MIC) improved the MIC of Compound 2 from 80 µg/ml to 1–2 µg/ml in wild type *C. albicans*, ketoconazole resistant *C. albicans*, and wild type *C. tropicalis* (FIG. 21). This synergy was not seen in an amphotericin-resistant strain. Subsequent experiments in a 2-way titration format confirmed the synergistic activity of the combination (FIG. 18). The synergy noted between these two agents was unique among the tested antifungal compounds, and was not noted for other promising compounds identified in the high throughput screen.

Figure 19:
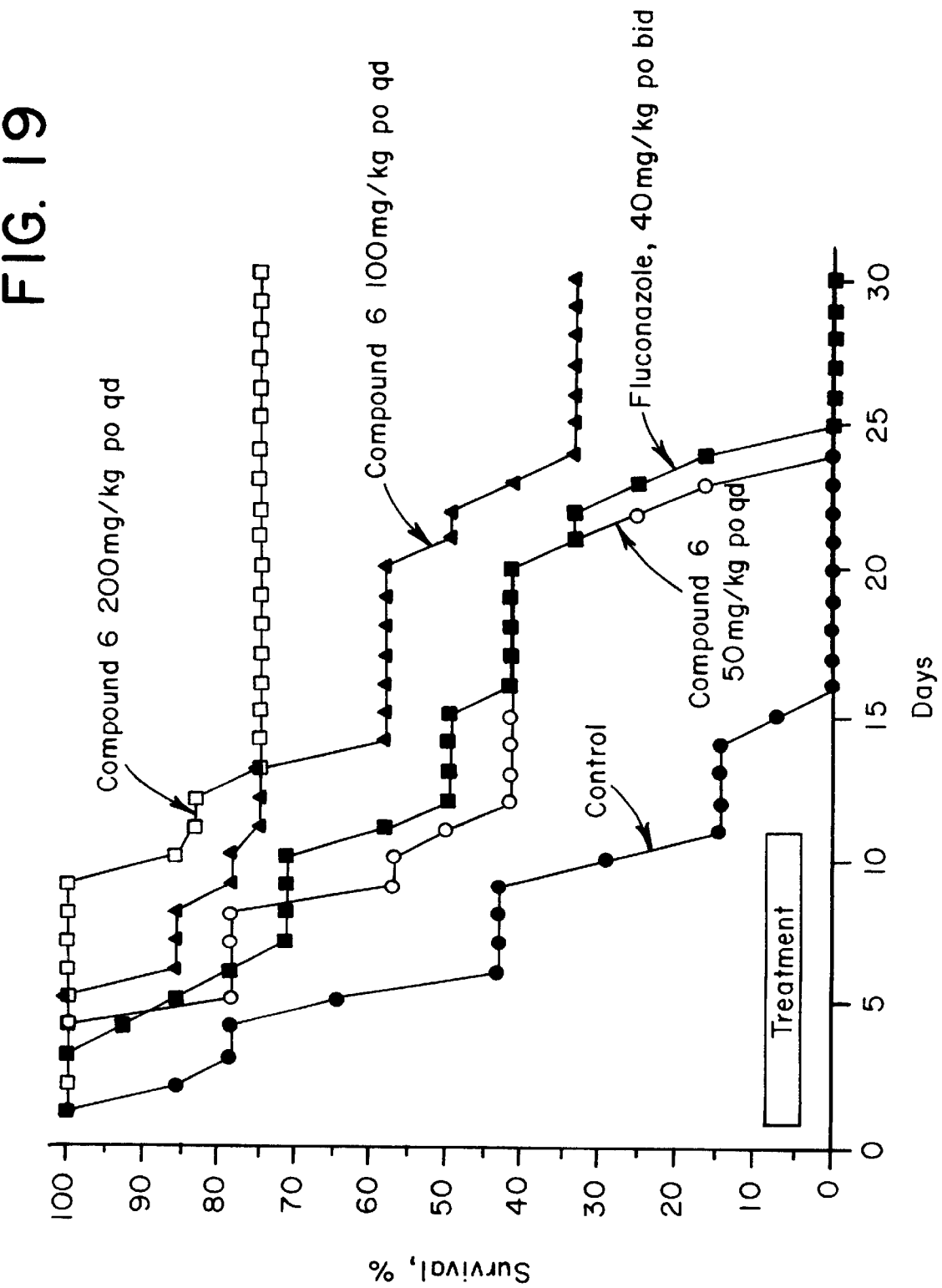
FIG. 19 illustrates the oral efficacy of Compound 6 in the treatment of mouse systemic candidiasis.
Figure 20:
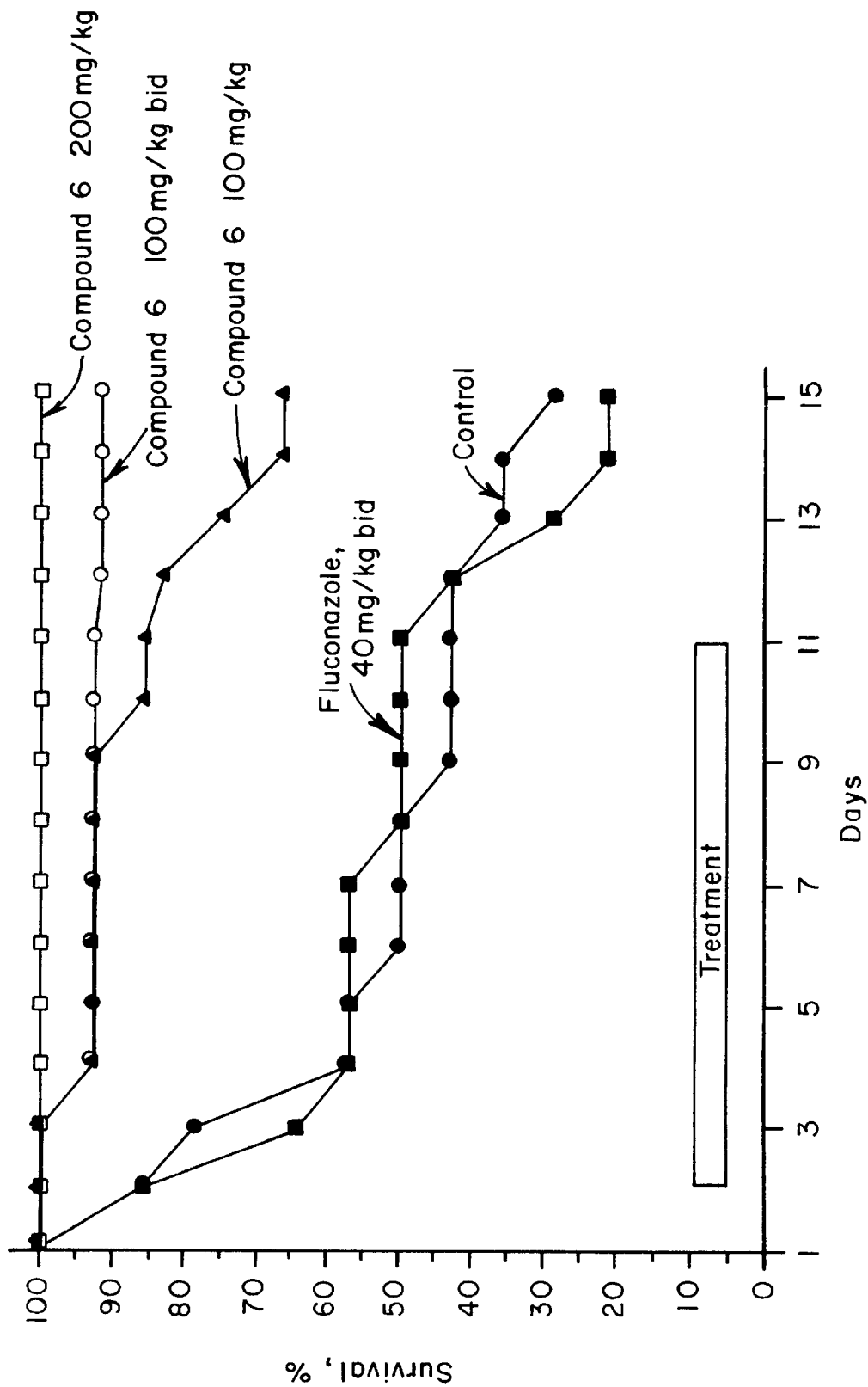
FIG. 20 illustrates activity of Compound 6 against fluconozole-resistant candidiasis.
Figure 22A:
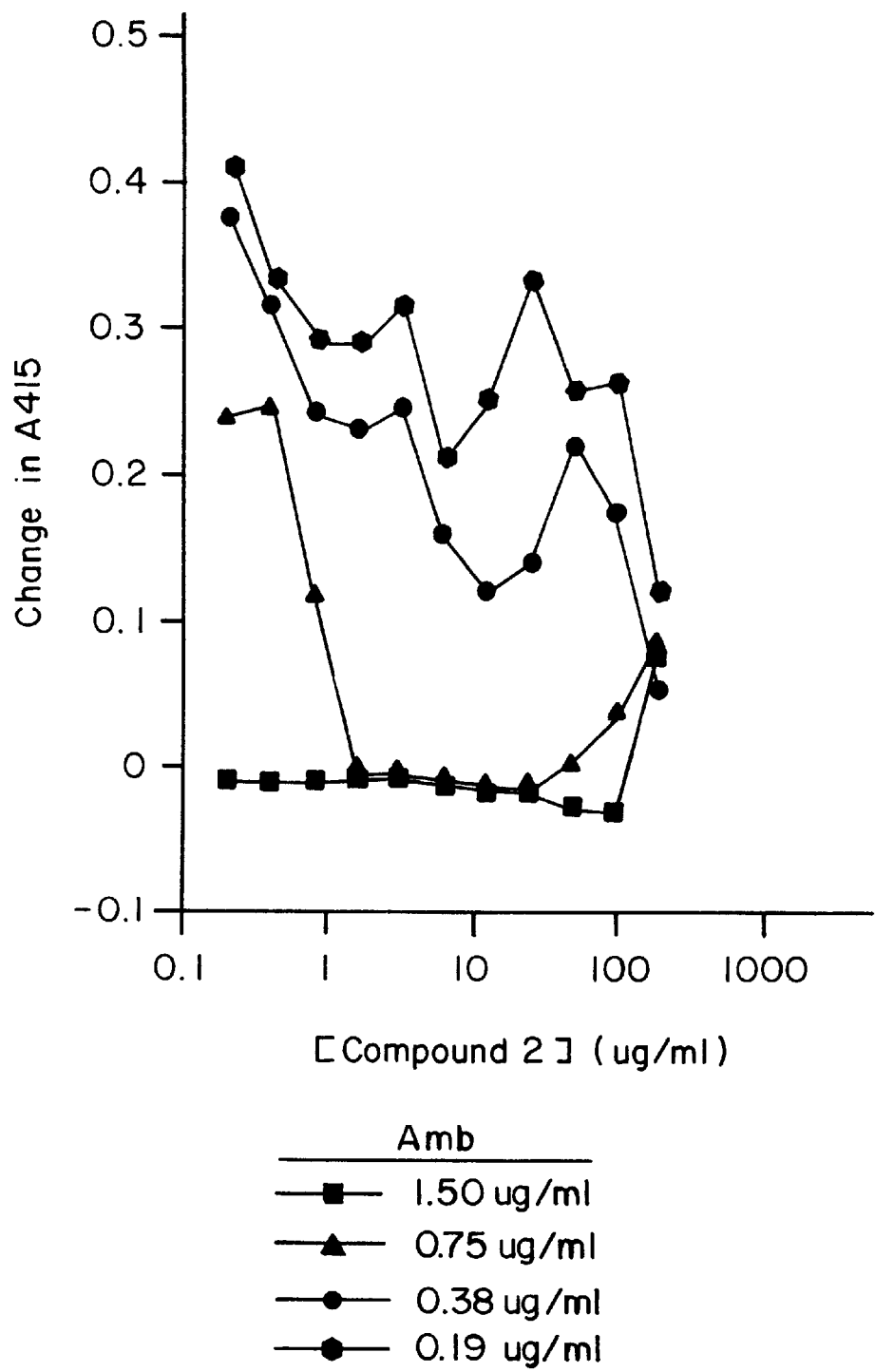
FIGS. 22A and 22B illustrate a two-way titration for synergy of Compound 2 with Am B.
Figure 22B:
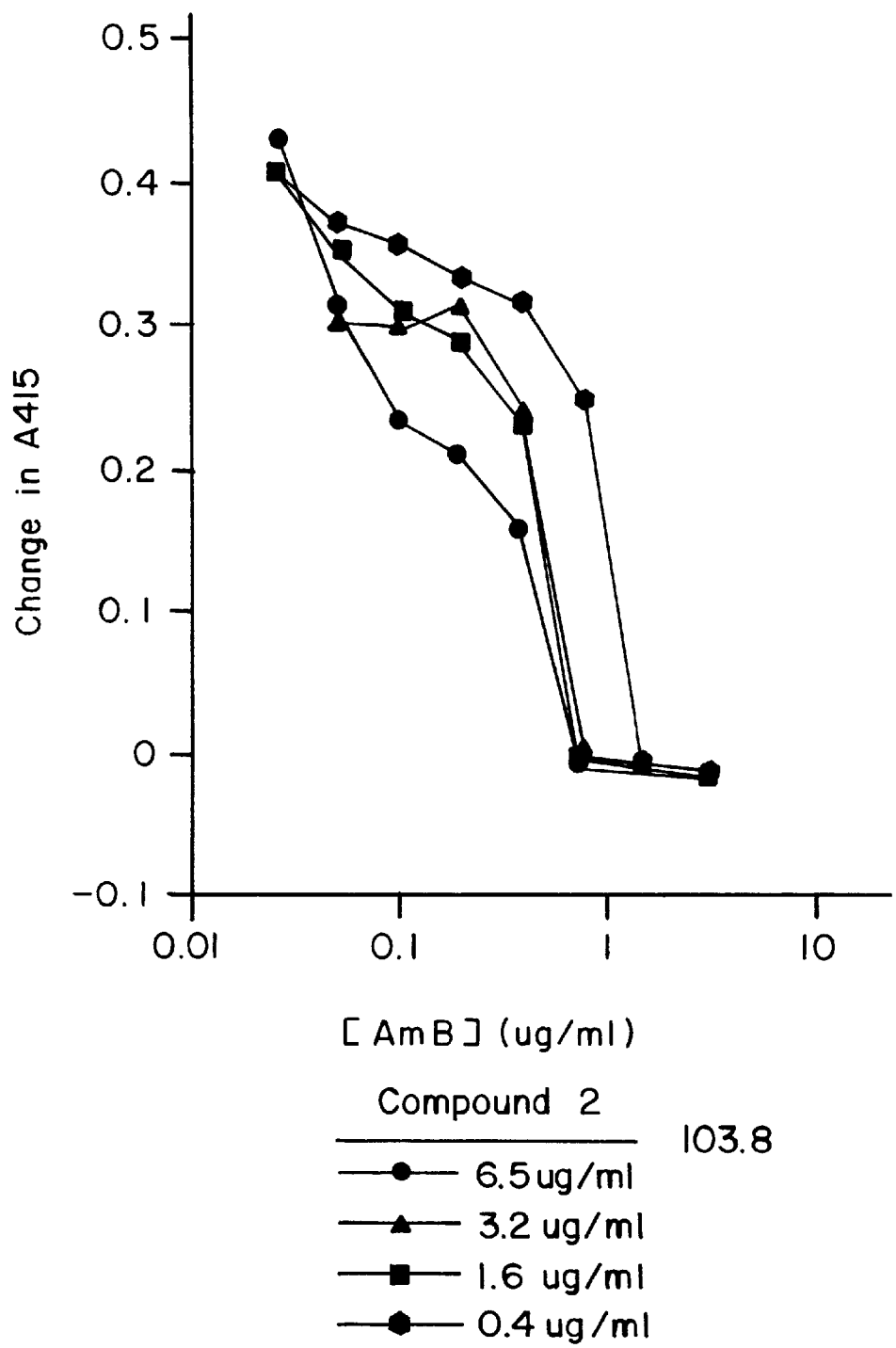
Figure 23:
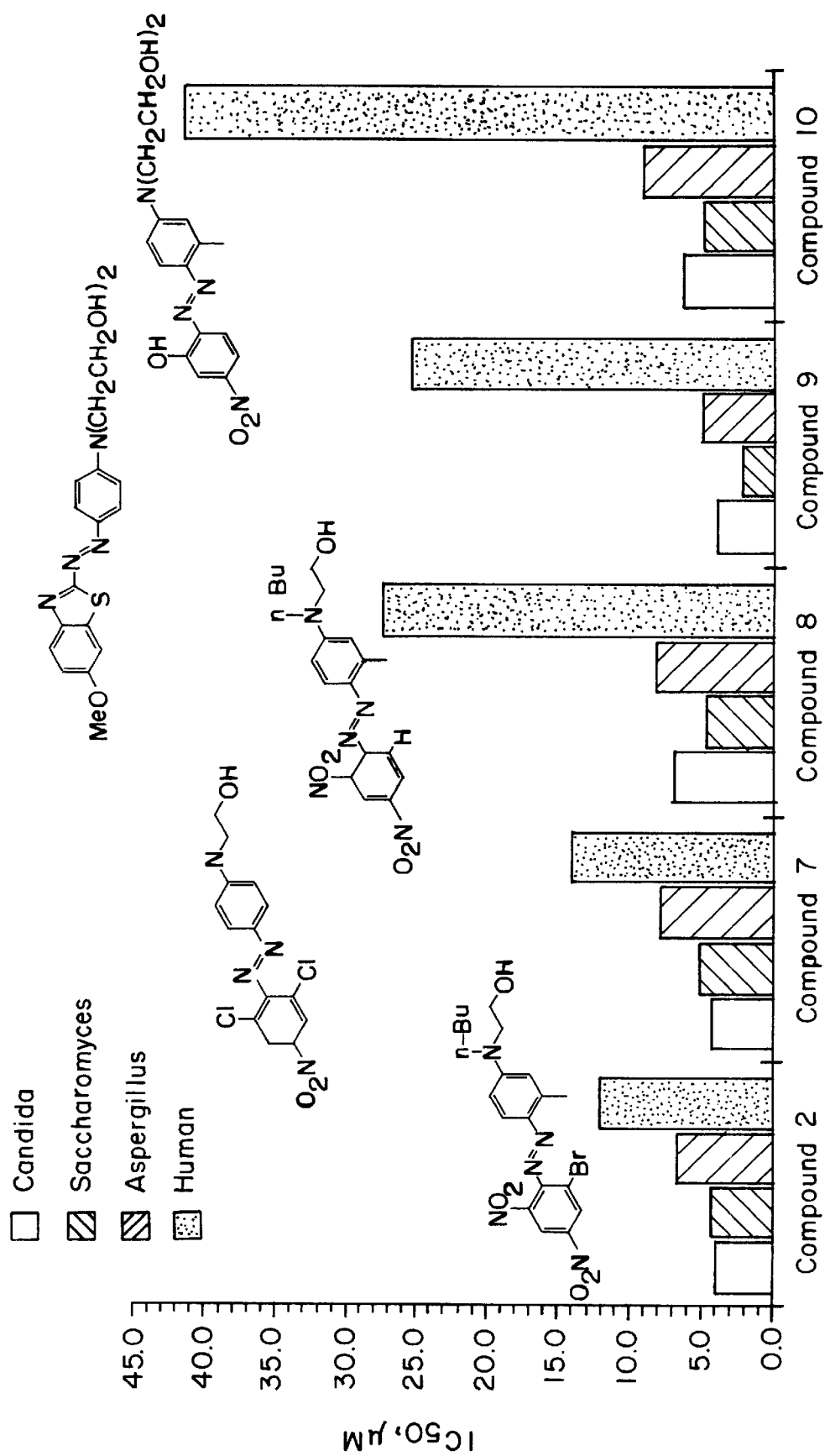
FIG. 23 illustrates increasing potency and specificity for Compound 2 and analogues thereof against fungal and human RNA polymerase II.
Figure 24:
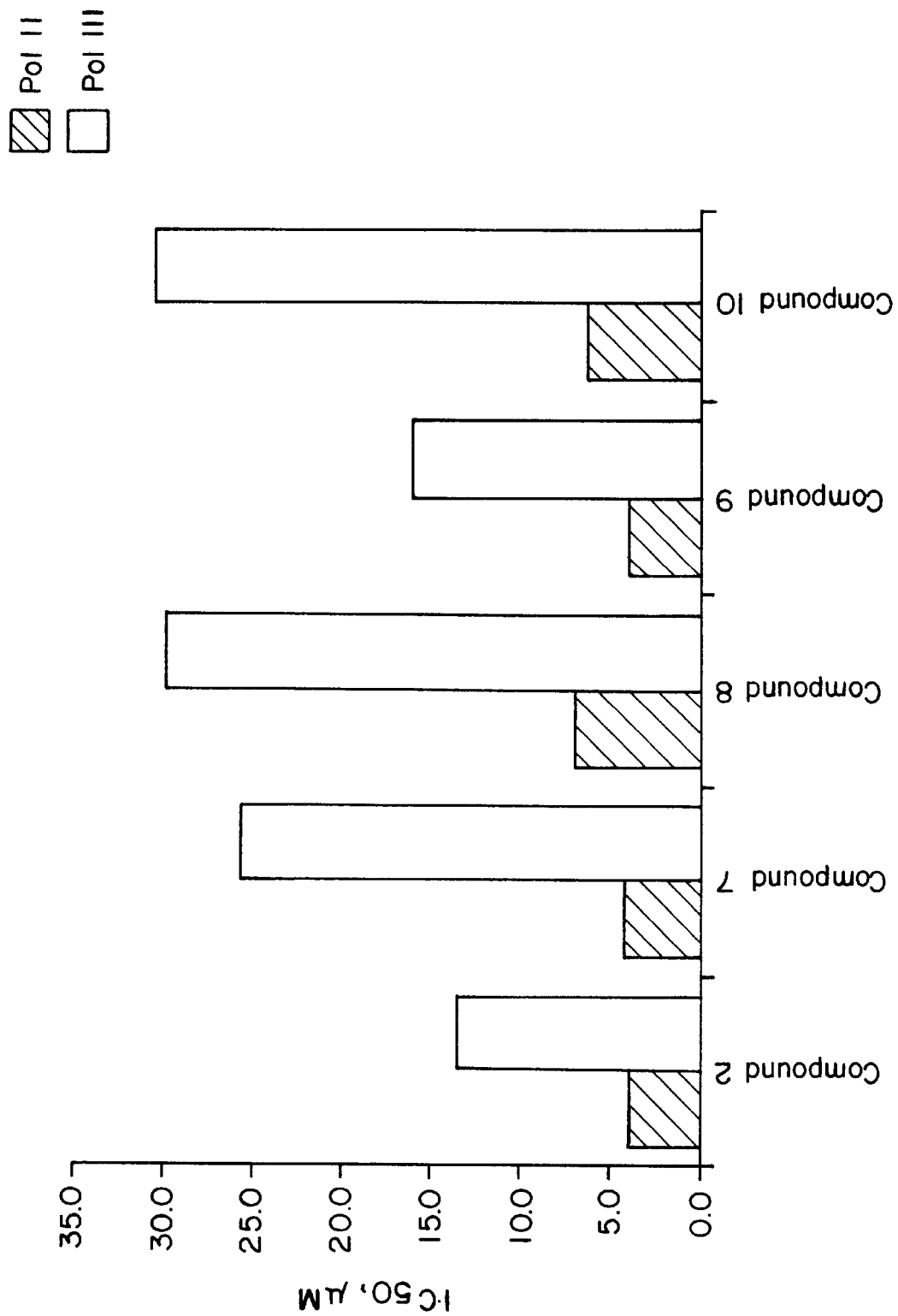
FIG. 24 illustrates polymerase II and III activity for Compound 2 and analogues thereof.

Analoging of Compound 2 produced a series of compounds with increased specificity to fungal RNA polymerases relative to the human enzyme (FIG. 19). These analogues retained specificity for Candida Pol II relative to Candida Pol III (FIG. 20). These analogues to Compound 2 and others have utility as single agents and in combination with amphotericin B.

Compound 2 is considered a lead compound in the antifungal program because differences in biological activity indicate a mechanism of action different from Compound 1 and Compound 6. The compound is fungistatic rather than fungicidal; it is the only member of the analogue class to exhibit synergy with amphotericin. MIC values of 1–2 μg/ml when used in combination with amphotericin B suggest potent intrinsic activity of the compound class.

The following are exemplary azo compounds of the invention:

(1) 4-[-2-[3-(trifluoromethyl)phenyl]diazenyl]-phenol;
(2) 3-[-2-[6-bromo-2,4-dinitrophenyl]diazenyl]-(4-(N-n-butyl, N-2-hydroxyethyl)-aniline;
(3) 4-[-2-[3-(trifluoromethyl)phenyl]diazenyl]-anisole;
(4) 4-[-2-[3-(trifluoromethyl)phenyl]diazenyl]-2-hydroxyphenol;
(5) 4-[-2-[3-(methyl)phenyl]diazenyl]-phenol;
(7) (4-[-2-[2-nitro-4-(trifluoromethyl)phenyl]diazenyl]-phenol;
(8) 4-[-2-[3-(trifluoromethyl)phenyl]diazenyl]-2-nitrophenol;
(9) 5-[-2-[3-(trifluoromethyl)phenyl]diazenyl]-2-hydroxybenzoic acid;
(10) 5-[(E)-2-[3-(trifluoromethyl)phenyl]diazenyl]-2-hydroxy-benzaldehyde
(11) 4-[-2-[3-(chloro)phenyl]diazenyl]phenol;
(12) 4-[-2-[3-(nitro)phenyl]diazenyl]phenol;
(13) 4-[-2-[2-fluoro-3-(trifluoromethyl)phenyl]diazenyl] phenol;
(14) 4-[-2-[4-fluoro-3-(trifluoromethyl-phenyl)diazenyl] phenol;
(15) 4-[-2-[6-fluoro-3-(trifluoromethyl)phenyl]diazenyl] phenol;
(16) 4-[-2-[3,5-(di-trifluoromethyl)phenyl]diazenyl]phenol;
(17) 4-[)-2-[3-(trifluoromethyl)-5-(metboxy)phenyl]diazenyl]pheno];
(18) 4-[-2-[3-(trifluoromethyl)phenyl]diazenyl]-2-cyanophenol;
(19) 4-[-2-[3-(tnfluoromethyl)phenyl]diazenyl]-2-(hydroxymethyl)-phenol;
(20) 4-[-2-[3-(trifluoromethyl)phenyl]diazenyl]-3-cyanophenol;
(21) 4-[-2-[3-(trifluoromethyl)phenyl]diazenyl]-3-(hydroxymethyl)-phenol;
(22) 4[-2-[3-(trifluoromethyl)phenyl]diazenyl]-3-methylphenol; and
(23) 4-[-2-[3-(trifluoromethyl]phenyl)diazenyl]-3-nitrophenol.

The following are exemplary stilbene compounds of the invention:

(6) 4-[-2-[3-(trifluoromethyl)phenyl]ethenyl]phenol;
(24) 4-[-2-[3-(trifluoromethyl)-phenyl]ethenyl]-anisole;
(25) 4-[-2-[3-(trifluorometbyl)phenyl]ethenyl]-methoxymethoxyl phenyl;
(26) 4-[-2-[3-(trifluoromethyl)phenyl]ethenyl]-2-bromophenol;
(27) 4[)-2-[3-(tifluoromethyl)phenyl]ethenyl]-2(dihydroxyboron)phenol; and
(28) 5-[-2-[3-(trifluoromethyl)phenyl]ethenyl]-2-hydroxy-(4-methylbenzoxy)-benzoate.

The exemplary stilbene compounds (6) and (24)–(28) are commercially available from Biofocus of Kent, England.

The following are exemplary benzamide compounds of the invention:

(29) 4-benzoxy-N-[3-(trifluoromethyl)phenyl]benzamide; and
(30) 4-hydroxy-N-[3-(trifnuoromethyl)phenyl]benzamide.

TABLE 1

Antifungal Activity of Stilbene, Ethano and Amide Isosteres of Compound 1.

| XY | IC$_{50}$ (μM) Candida pol II | IC$_{50}$ (μM) Human pol II | MIC (μg/mL) |
|---|---|---|---|
| N=N (1) | 10 | 43 | 16.6 |
| CH=CH (6) | 70 | 230 | 8.2 |
| CH$_2$CH$_2$ | 230 | >2000 | ND |
| NHCO | 27 | 82 | ND |
| CONH | 51 | 500 | ND |

TABLE 2

Pol II Activity of Compounds Related to Compound 1.

| XY | R1 | R2 | IC$_{50}$ (μM) Candida pol II | IC$_{50}$ (μM) Human pol II |
|---|---|---|---|---|
| N=N | 3-CF3 | 4-OH | 10 | 43 |
| N=N | 3-CF3 | 4-OMe | >2000 | >2000 |
| N=N | 3-CF3 | 2,4-diOH | 70 | 230 |
| N=N | 3-Me | 4-OH | 90 | 340 |
| N=N | 2-NO2-4-CF3 | 4-OH | 190 | 300 |
| N=N | 3-CF3 | 4-OH-3-NO2 | 103 | >2000 |
| N=N | 3-CF3 | 4-OH-3-COOH | 193 | 148 |
| N=N | 3-CF3 | 4-OH-3-CHO | 34 | 82 |
| CH=CH | 3-CF3 | 4-OMe | >2000 | >2000 |
| CH=CH | 3-CF3 | 4-OMOM | >2000 | >2000 |
| CH=CH | 3-CF3 | 4-OH-3-Br | 42 | 84 |
| CH=CH | 3-CF3 | 4-OH-3-B(OH)2 | 58 | 136 |
| CH=CH | 3-CF3 | 4-OH-3-COOMOB | >2000 | >2000 |
| NHCO | 3-CF3 | 4-OBn | >2000 | >2000 |

Bn = Benzyl, MOB = 4-methoxybenzyl, MOM = methoxymethyl

TABLE 3

Results of Screening of Azo Library (XY is N = N)

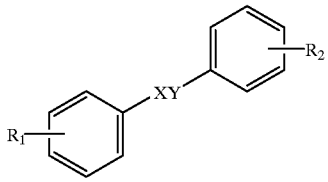

| R1 | R2 | % Inhibition (at 20 μM)* |
|---|---|---|
| 3-CF3 (Compound 1) | 4-OH | 59% |
| 3-Cl | 4-OH | 50% |
| 3-NO2 | 4-OH | 45% |
| 3-CF3-2-F | 4-OH | 38% |
| 3-CF3-4-F | 4-OH | 42% |
| 3-CF3-6-F | 4-OH | 39% |
| 3-CF3-5-CF3 | 4-OH | 28% |
| 3-CF3-5-OMe | 4-OH | 53% |
| 3-CF3 | 4-OH-3-CN | 37% |
| 3-CF3 | 4-OH-3-CH2OH | 33% |
| 3-CF3 | 4-OH-2-CN | 28% |
| 3-CF3 | 4-OH-2-CH2OH | 39% |
| 3-CF3 | 4-OH-2-Me | 42% |
| 3-CF3 | 4-OH-2-NO2 | 37% |

*Not active means less than −20% inhibition.

What is claimed is:

1. A pharmaceutical composition comprising a compound selected from the group consisting of
   4-[2-[3-(trifluoromethyl)phenyl]diazenyl]-phenol;
   3-[2-(6-bromo-2,4-dinitrophenyl)diazenyl]-(2-methyl-4-(N-n-butyl, N-2-hydroxyethyl)-aniline;
   4-[2-[3-(trifluoromethyl)phenyl]diazenyl]-anisole;
   4-[2-[3-(trifluoromethyl)phenyl]diazenyl]-2-hydroxyphenol;
   4-[2-[3-(methyl)phenyl]diazenyl]-phenol;
   (4-[2-[2-nitro-4-(trifluoromethyl)phenyl]diazenyl]-phenol;
   4-[2-[3-(trifluoromethyl)phenyl]diazenyl]-2-nitrophenol;
   5-[2-[3-(trifluoromethyl)phenyl]diazenyl]-2-hydroxybenzoic acid;
   5-[2-[3-(trifluoromethyl)phenyl]diazenyl]-2-hydroxybenzaldehyde
   4-[2-[3-(chloro)phenyl]diazenyl]phenol;
   4-[2-[2-fluoro-3-(trifluoromethyl)phenyl]diazenyl] phenol;
   4-[2-[4-fluoro-3-(trifluoromethyl-phenyl]diazenyl] phenol;
   4-[2-[6-fluoro-3-(trifluoromethyl)phenyl]diazenyl] phenol;
   4-[2-[3,5-(di-trifluoromethyl)phenyl]diazenyl]phenol;
   4-[2-[3-(trifluoromethyl)-5-(methoxy)phenyl]diazenyl] phenol;
   4-[2-[3-(trifluoromethyl)phenyl]diazenyl]-2-cyanophenol;
   4-[2-[3-(trifluoromethyl)phenyl]diazenyl]-2-(hydroxymethyl)-phenol;
   4-[2-[3-(trifluoromethyl)phenyl]diazenyl]-3-cyanophenol;
   4-[2-[3-(trifluoromethyl)phenyl]diazenyl]-3-(hydroxymethyl)-phenol;
   4-[2-[3-(trifluoromethyl)phenyl]diazenyl]-3-methylphenol;
   4-[2-[3-(trifluoromethyl]phenyl)diazenyl]-3-nitrophenol;
   4-benzoxy-N-[3-(trifluoromethyl)phenyl]benzamide; and
   4-hydroxy-N-[3-(trifluoromethyl)phenyl]benzamide;
   or a pharmaceutically acceptable salt thereof;
   and a pharmaceutically acceptable carrier.

2. The pharmaceutical composition of claim 1, wherein said compound is selected from the group consisting of
   4-[2-[3-(trifluoromethyl)phenyl]diazenyl]phenol; and
   3-[2-(6-bromo-2,4-dinitrophenyl)diazenyl]-(2-methyl-4-(N-n-butyl, N-2-hydroxyethyl)-aniline.

3. A method for inhibiting fungal replication, comprising contacting a microorganism with the pharmaceutical composition comprising a compound selected from the group consisting of
   4-[2-[3-(trifluoromethyl)phenyl]diazenyl]-phenol;
   3-[2-(6-bromo-2,4-dinitrophenyl)diazenyl]-(2-methyl-4-(N-n-butyl, N-2-hydroxyethyl)-aniline;
   4-[2-[3-(trifluoromethyl)phenyl]diazenyl]-anisole;
   4-[2-[3-(trifluoromethyl)phenyl]diazenyl]-2-hydroxyphenol;
   4-[2-[3-(methyl)phenyl]diazenyl]-phenol;
   (4-[2-[2-nitro-4-(trifluoromethyl)phenyl]diazenyl]-phenol;
   4-[2-[3-(trifluoromethyl)phenyl]diazenyl]-2-nitrophenol;
   5-[2-[3-(trifluoromethyl)phenyl]diazenyl]-2-hydroxybenzoic acid;
   5-[2-[3-(trifluoromethyl)phenyl]diazenyl]-2-hydroxybenzaldehyde
   4-[2-[3-(chloro)phenyl]diazenyl]phenol;
   4-[2-[3-(nitro)phenyl]diazenyl]phenol;
   4-[2-[2-fluoro-3-(trifluoromethyl)phenyl]diazenyl] phenol;
   4-[2-[4-fluoro-3-(trifluoromethyl-phenyl]diazenyl] phenol;
   4-[2-[6-fluoro-3-(trifluoromethyl)phenyl]diazenyl] phenol;
   4-[2-[3,5-(di-trifluoromethyl)phenyl]diazenyl]phenol;
   4-[2-[3-(trifluoromethyl)-5-(methoxy)phenyl]diazenyl] phenol;
   4-[2-[3-(trifluoromethyl)phenyl]diazenyl]-2-cyanophenol;
   4-[2-[3-(trifluoromethyl)phenyl]diazenyl]-2-(hydroxymethyl)-phenol;
   4-[2-[3-(trifluoromethyl)phenyl]diazenyl]-3-cyanophenol;
   4-[2-[3-(trifluoromethyl)phenyl]diazenyl]-3-(hydroxymethyl)-phenol;
   4-[2-[3-(trifluoromethyl)phenyl]diazenyl]-3-methylphenol;
   4-[2-[3-(trifluoromethyl]phenyl)diazenyl]-3-nitrophenol;
   4-benzoxy-N-[3-(trifluoromethyl)phenyl]benzamide; and
   4-hydroxy-N-[3-(trifluoromethyl)phenyl]benzamide;
   or a pharmaceutically acceptable salt thereof;
   and a pharmaceutically acceptable carrier.

4. A method of treating a subject suffering from a fungal disease, which comprises administering an amount of the pharmaceutical composition comprising a compound selected from the group consisting of 4-[2-[3-(trifluoromethyl)phenyl]diazenyl]-phenol;
3-[2-(6-bromo-2,4-dinitrophenyl)diazenyl]-(2-methyl-4-(N-n-butyl, N-2-hydroxyethyl)-aniline;
4-[2-[3-(trifluoromethyl)phenyl]diazenyl]-anisol;
4-[2-[3-(trifluoromethyl)phenyl]diazenyl]-2-hydroxy-phenol;
4-[2-[3-(methyl)phenyl]diazenyl]-phenol;
(4-[2-[2-nitro-4-(trifluoromethyl)phenyl]diazenyl]-phenol;
4-[2-[3-(trifluoromethyl)phenyl]diazenyl]-2-nitrophenol;
5-[2-[3-(trifluoromethyl)phenyl]diazenyl]-2-hydroxy-benzoic acid;
5-[2-[3-(trifluoromethyl)phenyl]diazenyl]-2-hydroxy-benzaldehyde
4-[2-[3-(chloro)phenyl]diazenyl]phenol;
4-[2-[3-(nitro)phenyl]diazenyl]phenol;
4-[2-[2-fluoro-3-(trifluoromethyl)phenyl]diazenyl] phenol;
4-[2-[4-fluoro-3-(trifluoromethyl-phenyl]diazenyl] phenol;
4-[2-[6-fluoro-3-(trifluoromethyl)phenyl]diazenyl] phenol;
4-[2-[3,5-(di-trifluoromethyl)phenyl]diazenyl]phenol;
4-[2-[3-(trifluoromethyl)-5-(methoxy)phenyl]diazenyl] phenol;
4-[2-[3-(trifluoromethyl)phenyl]diazenyl]-2-cyano-phenol;
4-[2-[3-(trifluoromethyl)phenyl]diazenyl]-2-(hydroxymethyl)-phenol;
4-[2-[3-(trifluoromethyl)phenyl]diazenyl]-3-cyano-phenol;
4-[2-[3-(trifluoromethyl)phenyl]diazenyl]-3-(hydroxymethyl)-phenol;
4-[2-[3-(trifluoromethyl)phenyl]diazenyl]-3-methyl-phenol;
4-[2-[3-(trifluoromethyl]phenyl)diazenyl]-3-nitro-phenol;
4-benzoxy-N-[3-(trifluoromethyl)phenyl]benzamide; and
4-hydroxy-N-[3-(trifluoromethyl)phenyl]benzamide;
or a pharmaceutically acceptable salt thereof;
and a pharmaceutically acceptable carrier.

5. A pharmaceutical composition comprising a compound of formula (I)

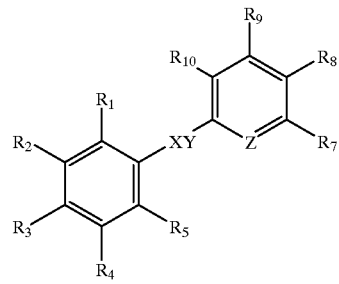

wherein XY is C=C; and

Z is CH, $R_1$, $R_3$, $R_4$, $R_5$, $R_7$, $R_9$, and $R_{10}$ are H, $R_2$ is $CF_3$ and $R_8$ is OH; or Z is CH, $R_1$, $R_3$, $R_4$, $R_5$, $R_7$, $R_9$, and $R_{10}$ are H, $R_2$ is $CF_3$ and $R_8$ is $OCH_3$; or Z is CH, $R_1$, $R_3$, $R_4$, $R_5$, $R_7$, $R_9$, and $R_{10}$ are H, $R_2$ is $CF_3$ and $R_8$ is $OCH_2OCH_3$; or Z is CH, $R_1$, $R_3$, $R_4$, $R_5$, $R_7$ and $R_{10}$ are H, $R_2$ is $CF_3$ and $R_8$ is OH and $R_9$ is Br; or Z is CH, $R_1$, $R_3$, $R_4$, $R_5$, $R_7$ and $R_{10}$ are H, $R_2$ is $CF_3$ and $R_8$ is OH and $R_9$ is $B(OH)_2$; or Z is CH, $R_1$, $R_2$, $R_4$, $R_5$, $R_7$ and $R_{10}$ are H, $R_2$ is $CF_3$ and $R_8$ is OH and $R_7$ is $COOCH_2O$-benzyl;

or a pharmaceutically acceptable salt thereof; and a pharmaceutically acceptable carrier.

6. A method for inhibiting fungal replication comprising contacting a microorganism with the pharmaceutical composition of claim 5.

7. A method of treating a subject suffering from a fungal disease, which comprises administering an amount of the pharmaceutical composition of claim 5.

* * * * *